(12) United States Patent
Martin et al.

(10) Patent No.: US 11,315,661 B2
(45) Date of Patent: Apr. 26, 2022

(54) METHODS AND SYSTEMS FOR PROVIDING EPITOPE TAGGED BIOMOLECULES

(71) Applicant: Becton, Dickinson and Company, Franklin Lakes, NJ (US)

(72) Inventors: Jody Martin, Encinitas, CA (US); Adam Wright, La Jolla, CA (US); Paul Waterman, San Clemente, CA (US); James Ghadiali, San Diego, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 602 days.

(21) Appl. No.: 15/886,763

(22) Filed: Feb. 1, 2018

(65) Prior Publication Data
US 2018/0232484 A1  Aug. 16, 2018

Related U.S. Application Data

(60) Provisional application No. 62/459,941, filed on Feb. 16, 2017.

(51) Int. Cl.
*G16B 50/00* (2019.01)
*G06F 16/248* (2019.01)
(Continued)

(52) U.S. Cl.
CPC ........... *G16B 50/00* (2019.02); *G06F 16/248* (2019.01); *G06F 16/2455* (2019.01); *G16B 30/00* (2019.02); *G16B 50/30* (2019.02)

(58) Field of Classification Search
CPC ........ G16B 30/00; G16B 50/30; G16B 99/00; G16B 50/00; G06F 16/248;
(Continued)

(56) References Cited

U.S. PATENT DOCUMENTS

2003/0022285 A1* 1/2003 Chirino .................. C07K 1/047
506/8
2003/0120432 A1* 6/2003 Zhou ...................... B82Y 30/00
702/20
(Continued)

FOREIGN PATENT DOCUMENTS

WO   WO200156216 A2   8/2001
WO   WO2013003752 A2  1/2013
WO   WO2017041016 A1  3/2017

OTHER PUBLICATIONS

Applied Biosystems, "Online Ordering Guide for TaqMan Gene Expression Assays", Retrieved from the Internet: URL:https:/fwww.garvan.org.au/research/capabilitiesjmolecular-genetics/documents/online-ordering-guide-for-taqman-gene-expression-assays.pdf, 2007, 6 pages.
(Continued)

*Primary Examiner* — Jesse P Frumkin
(74) *Attorney, Agent, or Firm* — Peter W. Schroen; Bret E. Field; Bozicbvic, Field & Francis LLP

(57) ABSTRACT

Aspects of the present disclosure include systems for use in preparing an epitope tagged biomolecule reagent. A reagent preparatory apparatus for preparing the epitope tagged biomolecule reagent from an activated biomolecule and activated epitope tag is also described. Methods for communicating and receiving an epitope tagged biomolecule reagent request and preparing the subject epitope tagged biomolecule reagents are also provided.

1 Claim, 7 Drawing Sheets

(51) Int. Cl.
*G06F 16/2455* (2019.01)
*G16B 30/00* (2019.01)
*G16B 50/30* (2019.01)

(58) Field of Classification Search
CPC ............ G06F 16/2455; C07K 2319/40; C12N 15/1065; G01N 33/6878; G06Q 10/087; G06Q 10/08
See application file for complete search history.

(56) References Cited

U.S. PATENT DOCUMENTS

| | | | |
|---|---|---|---|
| 2005/0240352 A1* | 10/2005 | Liang | G06Q 10/087 702/19 |
| 2006/0100788 A1* | 5/2006 | Carrino | G16H 10/40 702/19 |
| 2006/0257944 A1* | 11/2006 | Fridman | G16B 20/20 435/7.2 |
| 2012/0203567 A1* | 8/2012 | Seul | G06Q 10/06315 705/2 |
| 2013/0330335 A1 | 12/2013 | Bremel et al. | |

OTHER PUBLICATIONS

Applied Biosystems, "TaqMan Gene Expression Assays Protocol", Retrieved from the Internet: URL:http://www.ulab360.com/filesjprodfmanuals/2016G3/13/5541750G2.pdf, 2010.

\* cited by examiner

On Demand Epitope Tagged Biomolecules

REQUEST FORM

Format: [EPITOPE TAG ▼] ← 401A

Clone: [CD4 - RPA-T4 ▼] ← 401B

Quantity (Minimum 50µg): [50] ← 402

METHODS AND SYSTEMS FOR PROVIDING EPITOPE TAGGED BIOMOLECULES

CROSS-REFERENCE TO RELATED APPLICATIONS

This application claims priority to U.S. Provisional Patent Application Ser. No. 62/459,941 filed Feb. 16, 2017, the disclosure of which application is incorporated herein by reference.

INTRODUCTION

Assays for determining the presence and concentration of analytes in a biological fluid often rely on the specific binding of a probe compound. Depending on the analyte of interest, the probe compound may be a polypeptide, such as an antibody or binding fragment thereof, having a specific binding region. Assays that employ antibody or antibody derived probe compounds are often referred to as immunoassays.

Immunoassays can be configured as direct or indirect immunoassays. As illustrated in FIG. 1A, in direct immunoassays, the antibody specific reagent also includes a detectable label, such as a fluorophore. In contrast to direct immunoassays, indirect immunoassays employ sets of two or three immuno-reagents, which sets include a first target specific immuno-reagent and at least one additional anti-species specific immuno-reagent that binds to the target specific immuno-reagent, where at least one of the additional anti-species specific immuno-reagents is labeled, e.g., with a direct or indirectly detectable label. FIG. 1B provides an illustration of an indirect immunoassay. The purpose for these two or three immuno-reagent formats is two two-fold: 1) to associate a detectable label with the target analyte and to amplify any signal.[1] ≠[1]FIGS. 1A and 1B taken from www(dot)abcam(dot)com/secondary-antibodies/direct-vs-indirect-immunofluorescence

SUMMARY

Aspects of the present disclosure include systems for use in preparing an epitope tagged biomolecule reagent. Systems according to certain embodiments include an input manager for receiving a request for an epitope tagged biomolecule reagent, a memory for storing a dataset having a plurality of epitope tagged biomolecule reagent storage identifiers, a processing module communicatively coupled to the memory and configured to identify one or more epitope tagged biomolecule reagent storage identifiers from the dataset that corresponds to the epitope tagged biomolecule reagent request and an output manager for providing the one or more identified epitope tagged biomolecule reagent storage identifiers. A reagent preparatory apparatus for preparing the epitope tagged biomolecule reagent from an activated biomolecule and activated epitope tag is also described. Methods for communicating and receiving an epitope tagged biomolecule reagent request and preparing the subject epitope tagged biomolecule reagents are also provided.

Aspects of the invention include a fast, efficient and highly scalable process for delivering high quality and performance specific products across a wide range of biomolecule and epitope portfolios. In embodiments of the invention, a request for an epitope tagged biomolecule is made and in response to the request the epitope tagged biomolecule is prepared from a pre-existing collection of activated biomolecules and activated epitope tags. FIG. 2 provides an illustration of a method according to an embodiment of the invention. In FIG. 2, a collection of biomolecules (201a) and collection of epitope tags (201b) are first purified. (Step 201) Each biomolecule is then conjugated to a reactive linker to functionalize the biomolecules with a reactive moiety (i.e., activate the biomolecules with reactive linker L1, 202a). The collection of activated biomolecules is then purified and stored. Separately, a collection of epitope tags is also conjugated to reactive linkers to functionalize the collection of epitope tags with a reactive moiety (i.e., activate the epitopes with reactive linker L2, 202b). The collection of activated epitope tags is also purified and stored (Step 202). Upon request of an epitope tagged biomolecule reagent from a customer, a biomolecule is conjugated to an epitope tag by reacting an activated biomolecule (L1) with an activated epitope tag (L2) (Step 203) to form epitope tagged biomolecule (bonded through linkage L1-L2). In this way, any desired combination of biomolecule and epitope tag can be prepared on-demand by simply mixing an activated biomolecule with an activated epitope tag.

FIG. 3 illustrates this unique and new method of the present disclosure for providing customizable epitope tagged biomolecule reagents on-demand. A biomolecule of interest is purified (step 301) and then functionalized with a reactive linker (step 302) to produce an activated biomolecule 300a. Activated epitope tags 300b, 300c and 300d are separately prepared by functionalizing epitope tags with reactive linkers. Upon receipt of a request from a customer, any combination of activated biomolecule 300a and activated epitope tags 300b, 300c, 300d and 300e can be prepared on-demand by reaction of the reactive linker of activated biomolecule 300a with the reactive linkers of activated epitope tags 300b, 300c, 300d and 300e. Once conjugated, the epitope tagged biomolecules 300a-300b, 300a-300c, 300a-300d and 300a-300e are formulated into epitope tagged biomolecule reagent compositions and packaged for delivery to the customer.

Aspects of the present disclosure also include systems for use in preparing an epitope tagged biomolecule reagent. Systems according to certain embodiments include an input manager for receiving a request for an epitope tagged biomolecule reagent, a memory for storing a dataset having a plurality of epitope tagged biomolecule reagent storage identifiers, a processing module communicatively coupled to the memory and configured to identify one or more epitope tagged biomolecule reagent storage identifiers from the dataset that corresponds to the epitope tagged biomolecule reagent request and an output manager for providing the one or more identified epitope tagged biomolecule reagent storage identifiers. In some embodiments, the request for an epitope tagged biomolecule reagent includes a biomolecule request and an epitope tag request. In other embodiments, the request for an epitope tagged biomolecule reagent is an epitope tagged biomolecule request.

The input manager may be operatively coupled to a graphical user interface, such as a website menu interface where the request for an epitope tagged biomolecule reagent is entered into an internet website. In some embodiments, the input manager is configured to receive an epitope tagged biomolecule request. In other embodiments, the input manager is configured to receive a biomolecule request and an epitope tag request. The input manager may receive a plurality of epitope tagged biomolecule reagent requests, such as from a single user or from a plurality of users.

The subject systems include memory for storing one or more datasets that include storage identifiers for epitope tagged biomolecules, biomolecules, activated biomolecules, epitope tags, activated epitope tags and reactive linkers. Systems also include a processing module communicatively coupled to the memory that identifies a storage identifier from the one or more datasets that corresponds to the components (e.g., biomolecule request, epitope tag request, epitope tagged biomolecule request, etc.) of the epitope tagged biomolecule reagent request. In certain embodiments, an output manager is operatively coupled to a communication component to display the identified storage identifiers, such as on an electronic display or by printing the storage identifiers with a printer.

In certain embodiments, systems of interest further include a reagent preparatory apparatus in operative communication with the output manager for preparing an epitope tagged biomolecule reagent. The reagent preparatory manager is configured to receive the identified storage identifiers from the output manager and produce epitope tagged biomolecule reagent that corresponds to the epitope tagged biomolecule reagent request.

In embodiments, the reagent preparatory apparatus includes a plurality of activated biomolecules, a plurality of activated epitope tags and sampling device to provide an activated biomolecule and an activated epitope tag to a contacting apparatus. In certain instances, the reagent preparatory apparatus includes a reagent analyzer which may be used to characterize, formulate or purify the produced epitope tagged biomolecule reagent, such as by solid phase liquid chromatography.

The biomolecule may be a polypeptide, a nucleic acid or a polysaccharide. In certain embodiments, the biomolecule is a nucleic acid, such as an oligonucleotide, DNA or RNA. In other embodiments, the biomolecule is a polypeptide, such as a protein, an enzyme or an antibody. The term "epitope" is used in the context of the present application in its conventional sense to refer to a desired discrete site to which a secondary antibody of an indirect immunoassay specifically binds. An epitope tag is a molecular entity that includes a desired discrete site, i.e., epitope to which a secondary antibody of an indirect immunoassay specifically binds. The molecular entity that is the epitope tag may be any type of molecule, where molecular entities includes peptides, saccharides, nucleic acids, small molecules, etc.

The epitope tagged biomolecule reagents are prepared by coupling an activated biomolecule with an activated epitope tag. The activated biomolecule and activated epitope tag each include a reactive linker. In embodiments, the reactive linkers react to form a chemical linkage between the activated biomolecule and the activated linker.

Aspects of the present disclosure also include methods for preparing an epitope tagged biomolecule reagent. Methods according to certain embodiments include receiving a request for an epitope tagged biomolecule reagent, identifying a storage identifier that corresponds with the components of the epitope tagged biomolecule reagent request (e.g., storage identifiers corresponding to a biomolecule request and an epitope tag request) and outputting one or more identified storage identifiers. In some embodiments, the identified biomolecule storage identifier and epitope tag storage identifier is outputted onto an electronic display or is printed with a printer. In some embodiments, a plurality of requests for epitope tagged biomolecule reagents are received, such as from a single user or a plurality of users. In some instances, the request for the epitope tagged biomolecule reagent may include a plurality of biomolecule requests and a plurality of epitope tag requests. In other instances, the request for the epitope tagged biomolecule reagent may include a plurality of biomolecule requests and a single epitope tag request. In still other instances, the request for the epitope tagged biomolecule reagent may include a single biomolecule request and a plurality of epitope tag requests.

In certain embodiments, methods further include contacting an activated biomolecule with an activated epitope tag to produce an epitope tagged biomolecule reagent. In some embodiments, the activated biomolecule and activated epitope tag are contacted in a reagent preparatory apparatus. In some instances, the epitope tagged biomolecule reagent is further purified. After preparation, the epitope tagged biomolecule reagent may be packaged and transported to a remote location.

Aspects of the present disclosure also include methods for requesting and receiving an epitope tagged biomolecule reagent. Methods according to certain embodiments include communicating a request for an epitope tagged biomolecule reagent (e.g., to one of the subject systems described herein) and receiving an epitope tagged biomolecule reagent that includes a biomolecule bonded to epitope tag. In some embodiments, communicating a request for a epitope tagged biomolecule reagent includes inputting the biomolecule request and the epitope tag request into a graphical user interface, such as a website menu interface on an internet website. In some embodiments, communicating a request for an epitope tagged biomolecule reagent includes inputting a plurality of biomolecule requests and a plurality of epitope tag requests. In other embodiments, communicating a request for an epitope tagged biomolecule reagent includes inputting a single biomolecule request and a plurality of epitope tag requests. In yet other embodiments, communicating a request for an epitope tagged biomolecule reagent includes inputting a plurality of biomolecule requests and inputting a single epitope tag request. In still other embodiments, communicating a request for an epitope tagged biomolecule reagent includes inputting an epitope tagged biomolecule request.

BRIEF DESCRIPTION OF THE FIGURES

FIG. 4 depicts a graphical user interface for communicating a request for an epitope tagged biomolecule reagent according to certain embodiments of the invention.

DETAILED DESCRIPTION

Figure 1A:
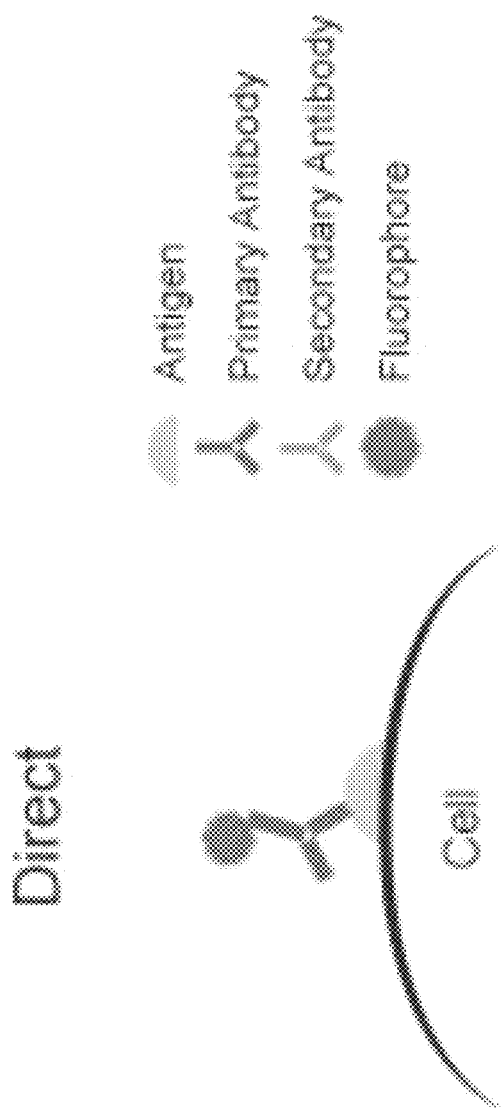
FIG. 1A provides an illustration of a direct immunoassay while FIG. 1B provides an illustration of an indirect immunoassay.
Figure 1B:
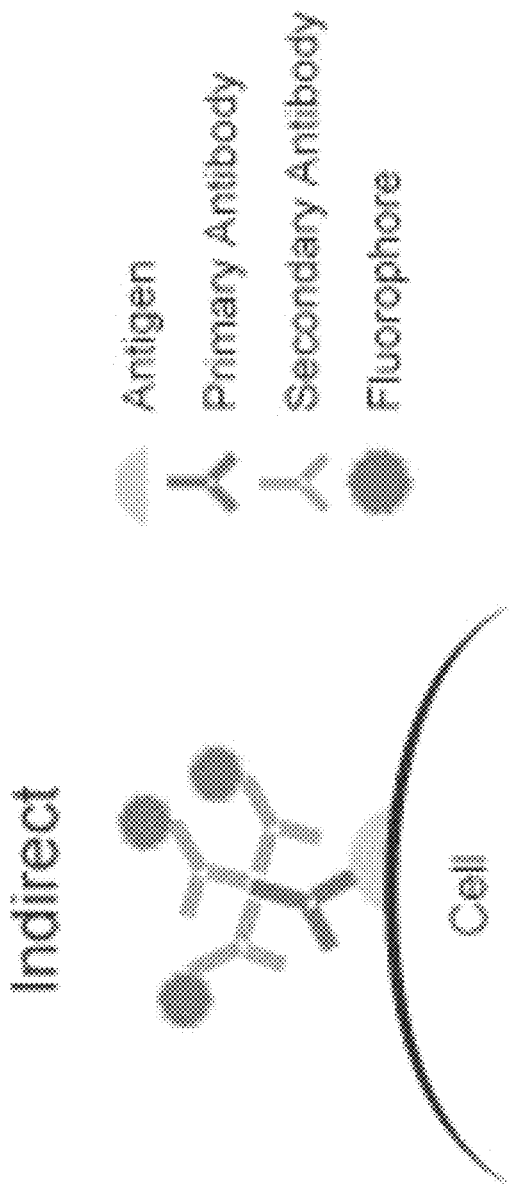
Figure 2:
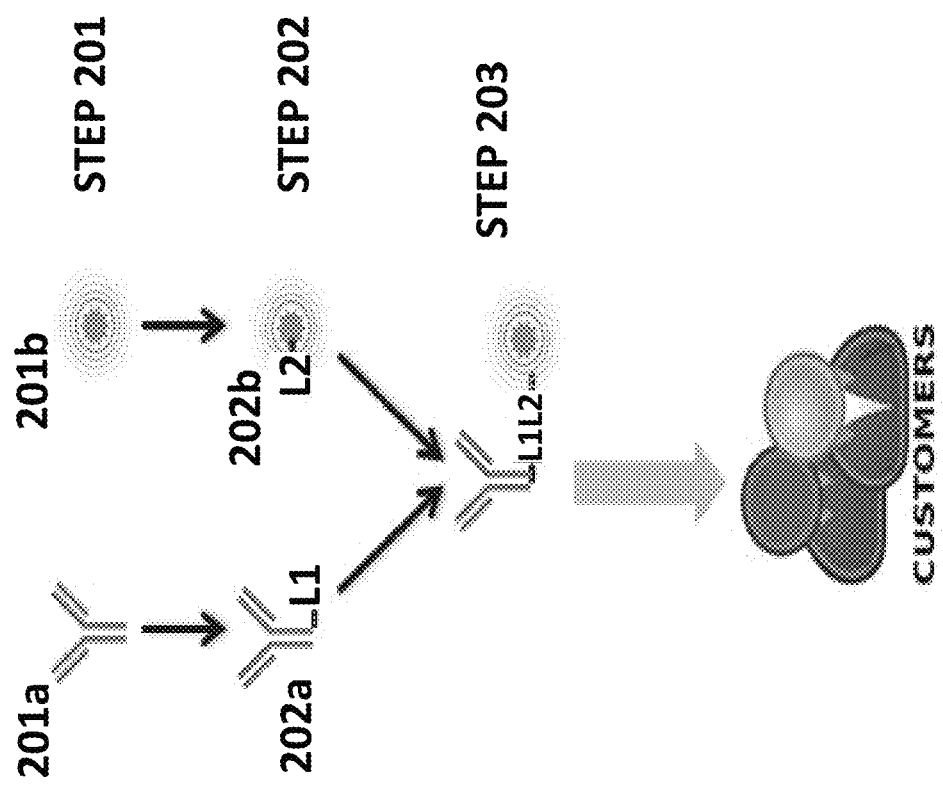
FIG. 2 provides an illustration of a method according to an embodiment of the invention.
Figure 3:
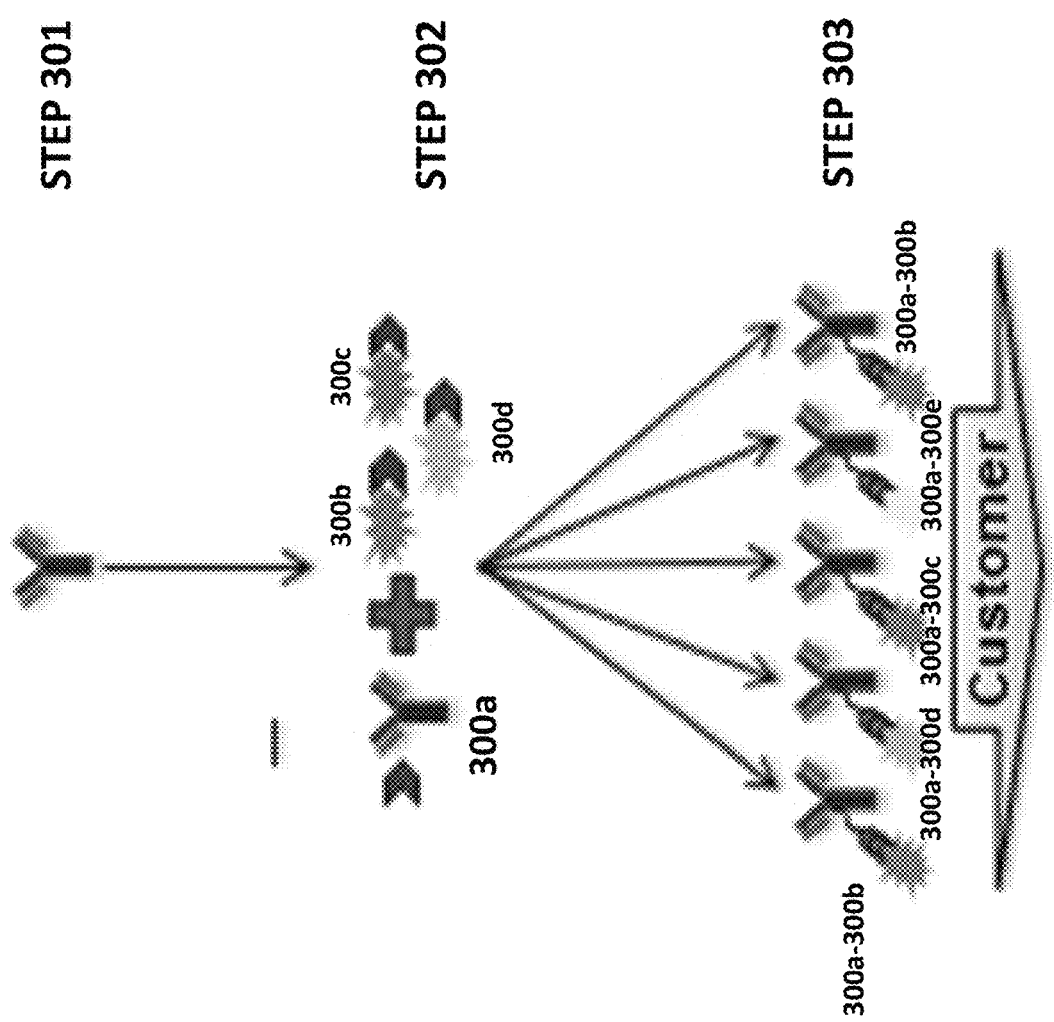
FIG. 3 illustrates a method of the present disclosure for providing customizable epitope tagged biomolecule reagents on-demand.

Aspects of the present disclosure include systems for use in preparing an epitope tagged biomolecule reagent. Systems according to certain embodiments include an input manager for receiving a request for an epitope tagged biomolecule reagent, a memory for storing a dataset having a plurality of epitope tagged biomolecule reagent storage identifiers, a processing module communicatively coupled to the memory and configured to identify one or more epitope tagged biomolecule reagent storage identifiers from the dataset that corresponds to the epitope tagged biomolecule reagent request and an output manager for providing the one or more identified epitope tagged biomolecule reagent storage identifiers. A reagent preparatory apparatus for preparing the epitope tagged biomolecule reagent from an activated biomolecule and activated epitope tag is also described. Methods for communicating and receiving an epitope tagged biomolecule reagent request and preparing the subject epitope tagged biomolecule reagents are also provided.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides systems for use in preparing an epitope tagged biomolecule reagent. In further describing embodiments of the disclosure, systems having an input manager for receiving an epitope tagged biomolecule reagent request and an output manager for providing biomolecule and epitope tag storage identifiers are first described in greater detail. Next, a reagent preparatory apparatus for preparing the epitope tagged biomolecule reagent from an activated biomolecule and an activated epitope tag are described. Methods for communicating and receiving an epitope tagged biomolecule reagent request and preparing the subject epitope tagged biomolecule reagents are also provided.

Systems for Use in Preparing an Epitope Tagged Biomolecule Reagent

Aspects of the present disclosure include systems for use in preparing an epitope tagged biomolecule reagent. Systems according to certain embodiments include an input manager for receiving a request for an epitope tagged biomolecule reagent, a memory for storing a dataset having a plurality of storage identifiers that correspond to the one or more components of the epitope tagged biomolecule reagent request (e.g., biomolecule, epitope tag, etc.), a processing module communicatively coupled to the memory and configured to identify a storage identifier from the dataset that corresponds to the components of the epitope tagged biomolecule reagent request and an output manager for providing the identified storage identifiers. As described in greater detail below, the term "epitope tagged biomolecule" reagent refers to a biological macromolecule coupled (e.g., through a covalent bond) to an epitope tag.

The biological macromolecule may be a biopolymer. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes DNA (including cDNA), RNA and oligonucleotides, regardless of the source. As such, biomolecules may include polysaccharides, nucleic acids and polypeptides. For example, the nucleic acid may be an oligonucleotide, truncated or full-length DNA or RNA. In embodiments, oligonucleotides, truncated and full-length DNA or RNA are comprised of 10 nucleotide monomers or more, such as 15 or more, such as 25 or more, such as 50 or more, such as 100 or more, such as 250 or more and including 500 nucleotide monomers or more. For example, oligonucleotides, truncated and full-length DNA or RNA of interest may range in length from 10 nucleotides to $10^8$ nucleotides, such as from $10^2$ nucleotides to $10^7$ nucleotides, including from $10^3$ nucleotides to $10^6$ nucleotides. In embodiments, biopolymers are not single nucleotides or short chain oligonucleotides (e.g., less than 10 nucleotides). By "full length" is meant that the DNA or RNA is a nucleic acid polymer having 70% or more of its complete sequence (such as found in nature), such as 75% or more, such as 80% or more, such as 85% or more, such as 90% or more, such as 95% or more, such as 97% or more, such as 99% or more and including 100% of the full length sequence of the DNA or RNA (such as found in nature)

Polypeptides may be, in certain instances, truncated or full length proteins, enzyme or antibodies. In embodiments, polypeptides, truncated and full-length proteins, enzymes or antibodies are comprised of 10 amino acid monomers or more, such as 15 or more, such as 25 or more, such as 50 or more, such as 100 or more, such as 250 or more and including 500 amino acid monomers or more. For example, polypeptides, truncated and full-length proteins, enzymes or antibodies of interest may range in length from 10 amino acids to $10^8$ amino acids, such as from $10^2$ amino acids to $10^7$ amino acids, including from $10^3$ amino acids to $10^6$ amino acids. In embodiments, biopolymers are not single amino acids or short chain polypeptides (e.g., less than 10 amino acids). By "full length" is meant that the protein, enzyme or antibody is a polypeptide polymer having 70% or more of its complete sequence (such as found in nature), such as 75% or more, such as 80% or more, such as 85% or more, such as 90% or more, such as 95% or more, such as 97% or more, such as 99% or more and including 100% of the full length sequence of the protein, enzyme or antibody (such as found in nature).

In some instances, the epitope tagged biomolecule reagent is an epitope tagged specific binding member. As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less.

The specific binding member can be proteinaceous. As used herein, the term "proteinaceous" refers to a moiety that is composed of amino acid residues. A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')$_2$, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a F(ab')$_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

In embodiments of the present disclosure, epitope tags are molecular entities that include a desired discrete site, i.e., epitope, to which a secondary antibody of an indirect immunoassay specifically binds. The molecular entity (i.e., epitope tag) that includes the epitope may be any type of molecule, where molecular entities of interest includes any of the biomolecules described above, e.g., peptides, saccharides, nucleic acids, small molecules, etc. In certain embodiments, the epitope tag is a polypeptide that includes a species-specific epitope such that, upon binding to a biomolecule in accordance with the invention, confers a species-specific epitope on the biomolecule. In such instances, the epitope tag may be a polypeptide ranging in size, ranging in some instances from 1 to 100,000, such as 5 to 1,000, including 5 to 100, e.g., 5 to 30 and including 5 to 20 residues in length. The species-specific epitope is, in some instances, an epitope found in antibodies to a particular antigen raised in a given species, such that it is an epitope found in antibodies raised in a given species to particular antibody. The species may vary, where examples of species include, but are not limited to, mouse, goat, rabbit, rat, horse, chicken, human, etc. The species-specific epitope may also be an epitope from a particular antibody isotype, e.g., IgG, IgA, IgM, IgD or IgE. The epitope tag that is bonded to a biomolecule reagent may be one that is chosen based on a desired secondary antibody, which secondary antibody may vary widely. Examples of secondary antibodies for which a given epitope tag may be selected for a given epitope tagged biomolecule reagent include, but are not limited to, anti-mouse, anti-goat, anti-rabbit, anti-rat, anti-horse, anti-chicken, anti-human, etc., secondary antibodies, where the secondary antibodies may be ones that bind to a particular isotype, e.g., IgG, IgA, IgM, IgD or IgE.

Systems may include an input manager for receiving an epitope tagged biomolecule reagent request. The epitope tagged biomolecule reagent request may include one or more components. In some instances, the epitope tagged biomolecule reagent request includes a single component and is an epitope tagged biomolecule request (i.e., a request for a biomolecule covalently bonded to an epitope tag through a linker, e.g., as described below). In other instances, the epitope tagged biomolecule reagent request includes two or more components. For example, the epitope tagged biomolecule reagent request may include a biomolecule request and an epitope tag request. In certain embodiments, the biomolecule request is an activated biomolecule request that includes a biomolecule and a reactive linker and the epitope tag request is an activated epitope tag request that includes an epitope tag and a reactive linker.

The phrases "epitope tagged biomolecule request", "biomolecule request" and "epitope tag request" are used herein to refer to information or data associated with a particular epitope tagged biomolecule, biomolecule or epitope/epitope tag, respectively. The request may include a string of one or more characters (e.g., alphanumeric characters), symbols, images or other graphical representation(s) associated with a particular epitope tagged biomolecule, biomolecule, epitope tag, activated biomolecule, activated epitope tag or reactive linker. In some instances, the request is a "shorthand" designation of the epitope tagged biomolecule, biomolecule, epitope tag, activated biomolecule, activated epitope tag or reactive linker. For example, the request may include an accession number or an abbreviated probe sequence. The request may also include descriptive information, such as chemical structure or reactivity. Information or data, in certain embodiments, may be any suitable identifier of the epitope tagged biomolecule, biomolecule or epitope tag and may include, but is not limited to, the name, monomer sequence, sequence identification number, ascension number or biological source of the biomolecule as well as the name, species reactivity, identity of secondary antibody, etc. of the epitope tag. With respect to the phrase epitope tag request, this request may include just information about the desired epitope (e.g., in the form of species, isotype, specific sequence, etc.) or also information about the epitope tag that includes the desired epitope, e.g., size of the molecule, etc.

As reviewed above, in some embodiments, the biomolecule is a biological probe for an analyte of interest and the biomolecule request includes information or data pertaining to a specific binding domain or specific binding member that binds to the analyte of interest. As reviewed above, specific binding domains or members of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

In some instances, the biomolecule is a polypeptide and the biomolecule request may include information such as polypeptide name, protein name, enzyme name, antibody name or the name of protein, enzyme or antibody fragments thereof, polypeptides derived from specific biological fluids (e.g., blood, mucus, lymphatic fluid, synovial fluid, cerebrospinal fluid, saliva, bronchoalveolar lavage, amniotic fluid, amniotic cord blood, urine, vaginal fluid and semen), polypeptides derived from specific species (e.g., mouse monoclonal antibodies) as well as amino acid sequence identification number.

In other instances, the biomolecule is a nucleic acid and the biomolecule request may include information such as oligonucleotide name, oligonucleotides identified by gene name, oligonucleotides identified by accession number, oligonucleotides of genes from specific species (e.g., mouse, human), oligonucleotides of genes associated with specific tissues (e.g., liver, brain, cardiac), oligonucleotides of genes associate with specific physiological functions (e.g., apoptosis, stress response), oligonucleotides of genes associated with specific disease states (e.g., cancer, cardiovascular disease) as well as nucleotide sequence.

As discussed above, epitope tags are molecular entities that include a desired discrete site, i.e., epitope, to which a secondary antibody of an indirect immunoassay specifically binds. The molecular entity (i.e., epitope tag) that includes the epitope may be any type of molecule, where molecular entities of interest includes any of the biomolecules described above, e.g., peptides, saccharides, nucleic acids, small molecules, etc. In certain embodiments, the epitope tag is a polypeptide that includes a species-specific epitope such that, upon binding to a biomolecule in accordance with the invention, confers a species-specific epitope on the biomolecule. In such instances, the epitope tag may be a polypeptide ranging in size, ranging in some instances from 1 to 100,000, such as 5 to 1,000, including 5 to 100, e.g., 5 to 30 and including 5 to 20 amino acid residues in length. The species-specific epitope is, in some instances, an epitope found in antibodies to a particular antigen raised in a given species, such that it is an epitope found in antibodies raised in a given species to particular antibody. The species may vary, where examples of species include, but are not limited to, mouse, goat, rabbit, rat, horse, chicken, human, etc. The species-specific epitope may also be an epitope from a particular antibody isotype, e.g., IgG, IgA, IgM, IgD or IgE. The epitope tag that is bonded to a biomolecule reagent may be one that is chosen based on a desired secondary antibody, which secondary antibody may vary widely. Examples of secondary antibodies for which a given epitope tag may be selected for a given epitope tagged biomolecule reagent include, but are not limited to, anti-mouse, anti-goat, anti-rabbit, anti-rat, anti-horse, anti-chicken, anti-human, etc., secondary antibodies, where the secondary antibodies may be ones that bind to a particular isotype, e.g., IgG, IgA, IgM, IgD or IgE.

The epitope tagged biomolecule reagent is prepared by coupling an activated biomolecule to an activated epitope tag. The term "activated" is used herein to refer to a biomolecule or epitope tag having a reactive linker or a reactive moiety that, when carried out under appropriate conditions, reacts with a second reactive linker or second reactive moiety to form a chemical linkage, such as for example, an ionic bond (charge-charge interaction), a non-covalent bond (e.g., dipole-dipole or charge-dipole) or a covalent bond. In some embodiments, the reactive linker or moiety of the activated biomolecule reacts with the reactive linker or moiety of the activated epitope tag to produce an ionic bond. In other embodiments, the reactive linker or moiety of the activated biomolecule reacts with the reactive linker or moiety of the activated epitope tag to produce a non-covalent bond. In yet other embodiments, the reactive linker or moiety of the activated biomolecule reacts with the reactive linker or moiety of the activated epitope tag to produce a covalent bond.

In certain embodiments, the reactive linker or moiety of the activated biomolecule reacts with the reactive linker or moiety of the activated epitope tag to produce a covalent bond. Any convenient protocol for forming a covalent bond between the reactive linker of the activated biomolecule and the reactive linker of the activated epitope tag may be employed, including but not limited to addition reactions, elimination reactions, substitution reactions, pericyclic reactions, photochemical reactions, redox reactions, radical reactions, reactions through a carbene intermediate, metathesis reaction, among other types of bond-forming reactions. In some embodiments, the activated biomolecule may be conjugated to the activated epitope tag through reactive linking chemistry such as where reactive linker pairs include, but is not limited to: maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate—periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[β-Maleimidopropionic acid]hydrazide.TFA)/thiol; azide/triarylphosphine; nitrone/cyclooctyne; azide/tetrazine and formylbenzamide/hydrazino-nicotinamide. In certain embodiments, the reactive linker of the activated biomolecule and the reactive linker of the activated epitope tag undergo a cycloaddition reaction, such as a [1+2]-cycloaddition, a [2+2]-cycloaddition, a [3+2]-cycloaddition, a [2+4]-cycloaddition, a [4+6]-cycloaddition, or cheleotropic reactions, including linkers that undergo a 1,3-dipolar cycloaddition (e.g., azide-alkyne Huisgen cycloaddition), a Diels-Alder reaction, an inverse electron demand Diels Alder cycloaddition, an ene reaction or a [2+2] photochemical cycloaddition reaction.

In certain embodiments, the biomolecule request and the epitope tag request include information or data pertaining to the reactive linker of the activated biomolecule and the activated epitope tag. For example, the biomolecule request and the epitope tag request may include information or data pertaining to the name of the reactive linker, a chemical structure, a structural description of the reactive linker or the reactive linker CAS number. In certain embodiments, the biomolecule request and the epitope tag request includes the name of reactive linker pairs, such as where the reactive linker pairs may be selected from maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate—periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[β-Maleimidopropionic acid]hydrazide.TFA)/thiol; azide/triarylphosphine; nitrone/cyclooctyne; azide/tetrazine and formylbenzamide/hydrazino-nicotinamide; a diene/a dienophile; and a 1,3-dipole/a dipolarophile.

The input manager is configured to receive the request for the epitope tagged biomolecule. To receive the epitope tagged biomolecule reagent request, the input manager is operatively coupled to a graphical user interface where one or more epitope tagged biomolecule reagents requests are entered. In certain instances, the epitope tagged biomolecule reagent request is entered on an internet website menu interface (e.g., at a remote location) and communicated to the input manager, over the internet or a local area network. In some embodiments, the input manager is configured receive a plurality of epitope tagged biomolecule reagent requests. For example, the input manager may be configured to receive 2 or more epitope tagged biomolecule reagent requests, such as 5 or more, such as 10 or more and including 25 or more epitope tagged biomolecule reagent requests.

Where the request for an epitope tagged biomolecule reagent includes only a single component and is an epitope tagged biomolecule request, the input manager may be configured to receive 2 or more epitope tagged biomolecule requests, such as 5 or more, such as 10 or more and including 25 or more epitope tagged biomolecule requests. Where the epitope tagged biomolecule reagent request includes two components, such as a biomolecule request and an epitope tag request, the input manager may be configured to receive 2 or more biomolecule requests, such as 5 or more, such as 10 or more and including 25 or more biomolecule requests and configured to receive 2 or more epitope tag requests, such as 5 or more, such as 10 or more and including 25 or more epitope tag requests. In some instances, the input manager is configured to receive an epitope tagged biomolecule reagent request that includes a single biomolecule request and single epitope tag request. In other instances, the input manager is configured to receive an epitope tagged biomolecule reagent request that includes a single biomolecule request and a plurality of different epitope tag requests. In yet other instances, the input manager is configured to receive an epitope tagged biomolecule reagent request that includes a plurality of different biomolecule requests and a single epitope tag request. In still other instances, the input manager is configured to receive an epitope tagged biomolecule reagent request that includes a plurality of different biomolecule requests and a plurality of different epitope tag requests. The input manager may be configured to receive epitope tagged biomolecule requests from a single user or a plurality of different users, such as 2 or more different users, such as 5 or more different users, such as 10 or more different users, such as 25 or more different users and including 100 or more different users.

In embodiments, the input manager is also configured to receive a quantity request corresponding to the desired amount of requested epitope tagged biomolecule reagent. The quantity request may be entered by typing a numerical and a unit (e.g., g, moles, μM, etc.) value into a text box, selecting a check box corresponding to the appropriate numerical and unit values or selecting a numerical value from a first drop-down menu and a unit value from a second drop-down menu.

In some embodiments, the input manager is operatively coupled to one or more searchable databases (e.g., catalog)

of epitope tagged biomolecules, activated biomolecules, biomolecules, activated epitope tags, epitope tags and reactive linkers. In certain instances, the input manager includes a database of epitope tagged biomolecules. In other instances, the input manager includes a database of activated biomolecules and activated epitope tags. In yet other instances, the input manager includes a database of biomolecules, epitope tags and reactive linkers.

All or part of each database of epitope tagged biomolecules, activated biomolecules, biomolecules, activated epitope tags, epitope tags and reactive linkers may be displayed on the graphical user interface, such as in a list, drop-down menu or other configuration (e.g., tiles). For example, the graphical user interface may display a list of each epitope tagged biomolecule, activated biomolecule, biomolecule, activated epitope tag, epitope tag and reactive linkers simultaneously (i.e., on a single screen) or may contain drop-down menus for each component of the epitope tagged biomolecule reagent request. In other embodiments, the epitope tagged biomolecule reagent request is provided by inputting information into appropriate text fields, selecting check boxes, selecting one or more items from a drop-down menu, or by using a combination thereof.

In one example, the graphical user interface includes a drop-down menu to input an epitope tagged biomolecule reagent request by selecting one or more epitope tagged biomolecules from the drop-down menu. In another example, the graphical user interface includes a first drop-down menu to input a biomolecule request and a second drop-down menu to input an epitope tag request by selecting one or more biomolecules and one or more epitopes or epitope tags from the first and second drop-down menus. In yet another example, the graphical user interface includes a first drop-down menu to input a biomolecule request, a second drop-down menu to input an epitope tag request and a third drop-down menu to input a reactive linker request by selecting one or more biomolecules, one or more epitope tags and one or more reactive linkers from the drop-down menus. In still another example, the graphical user interface includes a first drop down menu to input an activated biomolecule request and a second drop-down menu to input an activated epitope tag request by selecting one or more activated biomolecules and one or more activated linkers from the first and second drop-down menus.

In another example, the graphical user interface includes a list of epitope tagged biomolecules, activated biomolecules, biomolecules, activated epitope tags, epitope tags and reactive linkers that are available in the database. For example, the graphical user interface may display a list of each epitope tagged biomolecule, activated biomolecule, biomolecule, activated epitope tag, epitope tag and reactive linkers simultaneously on one or more screens or may contain drop-down menus for each component of the epitope tagged biomolecule reagent request. In some instances, a list of all available epitope tagged biomolecules, activated biomolecules, biomolecules, activated epitope tags, epitope tags and reactive linkers is displayed on a single page. In other instances, the list of all available epitope tagged biomolecules, activated biomolecules, biomolecules, activated epitope tags, epitope tags and reactive linkers displayed on a plurality of pages, such as 2 or more pages, such as 3 or more pages, such as 5 or more pages, such as 10 or more pages and including 25 or more pages. In yet other instances, the list of all available epitope tagged biomolecules, activated biomolecules, biomolecules, activated epitope tags, epitope tags and reactive linkers are each displayed in separate drop-down menus on a single page.

FIG. 4 depicts a graphical user interface for communicating a request for an epitope tagged biomolecule reagent according to certain embodiments. To communicate the epitope tagged biomolecule reagent request, a user inputs a biomolecule request and an epitope tag request onto Request form 400. The epitope tag request is inputted by selecting an epitope tag (e.g., for a given secondary immunoassay reagent, such as a labeled anti-species antibody or binding fragment thereof (e.g., rabbit IgG epitope tag for an anti-rabbit IgG labeled secondary antibody), from drop down menu 401A and the biomolecule request is inputted by selecting a biomolecule (e.g., an antibody probe) from drop-down menu 401B. Request form 400 also includes a text box for entering the quantity request 402 corresponding to the desired amount of epitope tagged biomolecule reagent in micrograms.

In certain embodiments, the input manager includes a search engine for searching for, adding or modifying epitope tagged biomolecule reagent requests and for responding to user queries (e.g., inputted into the graphical user interface locally or from a remote location over the internet or local area network). In some instances, each persistent object in the system memory has an associated table in a system database and object attributes are mapped to table columns. In a further aspect, each object has an object relational mapping file which binds that object to the table in the database. Objects are also associated with each other and this association is mapped as the relation between the tables. Objects are also associated with each other by many different relationships, such as one-to-one, one-to-many, many-to-one and many-to-many. Search criteria provided in user queries may include descriptions of attributes or properties associated with an object or by values corresponding to those attributes. Relationships may also be used as search criteria. Basic search criteria can depend upon an object's attributes and advanced search criteria can depend upon association of the object with other objects, e.g., by searching properties of related objects. In certain embodiments, search engines of interest include a finder framework, which will construct a plurality of searchable conditions (e.g., all possible queryable conditions). When a user specifies an entity or object to search for, the framework generates all possible search conditions for that object and then gives the result as per the conditions selected by the user.

Using the search engine, a user of the system can search for available epitope tagged biomolecules, biomolecules, activated biomolecules, epitope tags, activated epitope tags and reactive linkers. The search engine is also configured for searching for pending or completed epitope tagged biomolecule reagent requests. In addition, a user can use the search engine to inquire and find epitope tagged biomolecules, biomolecules, activated biomolecules, epitope tags, activated epitope tags and reactive linkers that may be of interest. For example, a user can search for a particular biomolecule that functions as a specific antigen probe or an epitope that is specifically bound by given secondary immunoassay reagent, such as a labelled anti-species specific antibody or binding fragment thereof. Search conditions may be different for different objects and in one instance, a generic finder framework gives a generic solution for such searching.

In certain embodiments, the search engine can build queries, save queries, modify queries, and/or update queries used to identify epitope tagged biomolecules, biomolecules, activated biomolecules, epitope tags, activated epitope tags or reactive linkers. In some instances, the search results can be shared, compared or modified. In certain instances, systems are configured to set a maximum of search results that fit a search criteria to be displayed on the graphical user interface. In some embodiments, search results are displayed on a Webpage which includes capabilities for allowing possible actions. Such capabilities can include, but are not limited to, links, buttons, drop down menus, fields for receiving information from a user, and the like. In certain aspects, the system further includes a result formatter for formatting search results (e.g., to build appropriate user interfaces such as Web pages, to specify links, provide a way to associate actions (e.g., "delete," "edit," etc.) with images, text, hyperlinks and/or other displays.

The system may also display the search criteria for an object under search on the web page. In one aspect, the system takes input data from the finder framework and creates a web page dynamically showing the search criteria for that object. In another aspect, the finder framework creates all possible queryable conditions for the object under search. These conditions are displayed on search web page as different fields. A user can select or specify value(s) for these field(s) and execute a search. The fields that are to be displayed have their labels in localized form. Fields may be in the form of a "select" box, or a text box or other area for inputting text. For example, a user may desire to search for a biomolecule. Biomolecules in the searchable database include queryable conditions such as compound name or sequence number (e.g., accession number).

In one embodiment, the search engine supports searching for each of the epitope tagged biomolecules, biomolecules, activated biomolecules, epitope tags, activated epitope tags and reactive linkers in the database. In some instances, the system provides a generic finder framework to create all queryable conditions for an object under search. Such conditions will generally depend upon the properties of the object and its relationship(s) with other objects. In other embodiments, the finder framework retrieves localized field names for these conditions and their order and stores these in the system memory (e.g., in an objectdefinition.xml file). In one example, fields are displayed on a search page in the order in which they are stored in a file as a set of search parameters for which a user can select or enter values. The search parameters may be in the form of a list of objects and the parameters may relate to attribute categories. For example, in response to a user searching for an epitope tagged biomolecule, the system may display the queryable conditions: "name of epitope tagged biomolecule," "keywords used for search," "created by," "modified by," "modification date," "annotation" and the like. The finder framework can return the queryable conditions in the form of a collection, which can be displayed on a search page, which lists or represents the various search fields corresponding to the attribute categories in a localized form. A user may enter values for these fields and perform, e.g., selecting one or more of an epitope tagged biomolecule, biomolecule, activated biomolecule, epitope tag, activated epitope tag and reactive linker having a specific name, structure, registry number, etc., providing specific keywords, identifying a desired domain, creator, modification date, annotation, and the like. The system then displays a list of epitope tagged biomolecules, biomolecules, activated biomolecules, epitope tags, activated epitope tags or reactive linkers that satisfy the search conditions. In certain embodiments, the system displays information regarding the criteria used to perform the search.

In certain embodiments, the input manager includes an epitope tagged biomolecule design platform which is configured to provide a recommendation for choosing one or more biomolecules, activated biomolecules, epitope tags, activated epitope tags or reactive linkers. In some instances, the design platform is configured to provide a recommendation for choosing one or more biomolecules, activated biomolecules, epitope tags, activated epitope tags or reactive linkers based on user input of one or more parameters of the desired epitope tagged biomolecule. For example, parameters of the desired epitope tagged biomolecule which may be inputted by the user into the design platform may include, but are not limited to, desired physical properties of the epitope tagged biomolecule (e.g., molecular mass, melting point, purity, etc.); desired chemical properties of the epitope tagged biomolecule (e.g., chemical structure, structural similarity to a second epitope tagged biomolecule, ionizability, solvation, hydrolysis, chemical reactivity, enzymatic reactivity, binding affinity, etc.); spectroscopic properties (e.g., absorbance wavelength range, absorbance maxima, emission wavelength range, emission maxima, Stokes shift, quantum yield, molar extinction coefficient, etc.) In other instances, the design platform is configured to provide a recommendation for choosing one or more biomolecules, activated biomolecules, epitope tags, activated epitope tags or reactive linkers based on the application of the epitope tagged biomolecule. For example, the design platform may be configured to provide a recommendation for choosing each component of the epitope tagged biomolecule based on instruments that will be used (e.g., flow cytometer, fluorescence spectrometer, etc.), instrument configuration, nature of secondary immunoassay reagents, as well as experimental parameters (e.g., target abundance such as antigen density on a cell). The graphical user interface may include one or more text input fields or drop-down menus for inputting data used by the design platform to provide a recommendation for choosing one or more biomolecules, activated biomolecules, epitope tags, activated epitope tags or reactive linkers.

The epitope tagged biomolecule design platform may be configured to provide a recommendation for a plurality of different biomolecules, activated biomolecules, epitope tags, activated epitope tags or reactive linkers based on information (e.g., properties of the epitope tagged biomolecule or expected application of the epitope tagged biomolecule) inputted by the user. For example, the design platform may be configured to recommend 2 or more different biomolecules, activated biomolecules, epitope tags, activated epitope tags or reactive linkers based on information inputted by the user, such as 3 or more, such as 4 or more, such as 5 or more, such as 10 or more and including 25 or more biomolecules, activated biomolecules, epitope tags, activated epitope tags or reactive linkers.

In certain embodiments, the epitope tagged biomolecule design platform is configured to provide a recommendation as to the combination of biomolecule, epitope tag, activated epitope tag or reactive linker that is best suited for a particular application (e.g., specific secondary immunoassay reagents). For example, the design platform may be configured such that a user enters a list of one or more biomolecules and one or more epitope tags as well as application information (e.g., secondary immunoassay reagent(s) to be employed, instrument configuration, target abundance, etc.) and the design platform outputs combinations a recommendation of biomolecules, epitope tags, activated epitope tags and reactive linkers best suited for the stated application. In certain embodiments, the recommendation for an epitope tagged biomolecule, biomolecule, activated biomolecule, epitope tag, activated epitope tag or reactive linker is displayed on a display (e.g., an electronic display) or may be printed with a printer, such as onto a human (paper) readable medium or in a machine readable format (e.g., as a barcode). In other embodiments, the recommendation for an epitope tagged biomolecule, biomolecule, activated biomolecule, epitope tag, activated epitope tag or reactive linker may be communicated to the input manager and the recommended epitope tagged biomolecule may be prepared as described above.

Systems of the present disclosure also include a memory for storing a dataset having a plurality of storage identifiers that correspond with the components the of the epitope tagged biomolecule reagent request. The term "memory" is used herein in its conventional sense to refer to a device that stores information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices). The memory may be a computer readable medium or permanent memory. In embodiments, the memory may include one or more datasets having a plurality of storage identifiers that correspond to each epitope tagged biomolecule, biomolecule, epitope tag, activated biomolecule, activated epitope tag and reactive linker in the system database.

The datasets stored in the memory include storage identifiers that correspond with each epitope tagged biomolecule, biomolecule, epitope tag, activated biomolecule, activated epitope tag or reactive linker. The storage identifiers may be presented in the dataset as a string of one or more characters (e.g., alphanumeric characters), symbols, images or other graphical representation(s) associated with a particular epitope tagged biomolecule, biomolecule, epitope tag, activated biomolecule, activated epitope tag or linker. In some instances, the storage identifier is abbreviated designation of the epitope tagged biomolecule, biomolecule, epitope tag, activated biomolecule, activated epitope tag or linker. For example, the storage identifier may include references to accession number, sequence identification number, identifiable probe sequence, species, or may be a custom identification code.

The number of storage identifiers in each dataset stored in memory may vary, depending on the type of storage identifiers. For example, the dataset stored in memory having a plurality of epitope tagged biomolecule storage identifiers may include 10 or more epitope tagged biomolecule storage identifiers, such as 25 or more, such as 50 or more, such as 100 or more identifiers, such 250 or more, such as 500 or more and including 1000 or more epitope tagged biomolecule storage identifiers. The dataset stored in memory having a plurality of biomolecules or activated biomolecules may include 25 or more biomolecule or activated biomolecule storage identifiers, such as 50 or more, such as 100 or more, such as 250 or more, such as 500 or more and including 1000 or more biomolecule or activated biomolecule storage identifiers. The dataset stored in memory having a plurality of epitope tags or activated epitope tags may include 5 or more epitope tag or activated epitope tag storage identifiers, such as 10 or more, such as 15 or more, such as 25 or more and including 50 or more epitope or activated epitope tag storage identifiers. In certain embodiments, the dataset stored in memory having a plurality of reactive linkers includes 2 or more reactive linker storage identifiers, such as 3 or more, such as 5 or more, such as 10 or more and including 15 or more reactive linker storage identifiers.

The memory is in operative communication with a processing module that identifies one or more storage identifiers from the dataset that corresponds to the request received by the input manager. In some embodiments, the request for an epitope tagged biomolecule reagent is an epitope tagged biomolecule request and the processing module identifies an epitope tagged biomolecule storage identifier from a dataset in the memory having a plurality of epitope tagged biomolecules storage identifiers. In other embodiments, the request for an epitope tagged biomolecule reagent includes a biomolecule request and an epitope request and the processing module identifies: 1) a biomolecule storage identifier from a first dataset in the memory having a plurality of biomolecule storage identifiers; and 2) an epitope tag storage identifier from a second dataset in the memory having a plurality of epitope tag storage identifiers. In still other embodiments, the request for an epitope tagged biomolecule reagent includes a biomolecule request, an epitope tag request and a reactive linker request and the processing module identifies: 1) a biomolecule storage identifier from a first dataset in the memory having a plurality of biomolecule storage identifiers; 2) an epitope tag storage identifier from a second dataset in the memory having a plurality of epitope tag storage identifiers; and 3) a reactive linker storage identifier from a third dataset in the memory having a plurality of reactive linker storage identifiers.

When a particular storage identifier that corresponds to an epitope tagged biomolecule request, biomolecule request, epitope tag request, activated biomolecule request, activated epitope tag request or reactive linker request are not available (i.e., cannot be identified by the processing module from any dataset in the memory), the memory may include algorithm for providing a recommendation for an alternative epitope tagged biomolecule, biomolecule, epitope tag, activated biomolecule, activated epitope tag or reactive linker. The recommendation may be based on similarities in chemical structure, reactivity, probe target, binding affinity, target abundance, target density, size, price, etc. as the requested epitope tagged biomolecule, biomolecule, epitope tag, activated biomolecule, activated epitope tag or reactive linker. The memory may be configured to provide a recommendation for one or more alternatives, such as 2 or more alternatives, such as 3 or more alternatives and including 5 or more alternatives, depending on the similarity between the requested component and available epitope tagged biomolecule, biomolecule, epitope tag, activated biomolecule, activated epitope tag or reactive linkers.

The processing module may include a commercially available processor such as a processor made by Intel Corporation, a SPARC® processor made by Sun Microsystems, or it may be one of other processors that are or will become available.

The processor executes the operating system, which may be, for example, a WINDOWS®-type operating system from the Microsoft Corporation; a Unix® or Linux-type operating system or a future operating system; or some combination thereof. The operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

Processing modules of the subject systems include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include WINDOWS NT®, Sun Solaris™, Linux®, OS/400®, Compaq Tru64 Unix®, SGI RIX®, Siemens Reliant Unix®, and others. Other development products, such as the Java™ 2 platform from Sun Microsystems, Inc. may be employed in processors of the subject systems to provide suites of applications programming interfaces (API's) that, among other things, enhance the implementation of scalable and secure components. Various other software development approaches or architectures may be used to implement the functional elements of system and their interconnection, as will be appreciated by those of ordinary skill in the art.

Systems of the present disclosure also include an output manager that provides the identified storage identifiers from the processing module. In some embodiments, the output manager includes an electronic display and the identified storage identifiers are outputted onto the electronic display. One or more storage identifiers may be outputted onto the electronic display simultaneously, such as 2 or more, such as 3 or more, such as 5 or more, such as 10 or more, such as 25 or more, such as 100 or more and including 500 or more storage identifiers. The output manager may display the storage identifiers of the epitope tagged biomolecule reagent requests from a single user or from a plurality of users, such as from 2 or more users, such as 5 or more users, such as 10 or more users, such as 25 or more users and including 100 or more users. The output manager may be configured to organize the displayed storage identifiers, as desired, such as grouping the storage identifiers according to each request for an epitope tagged biomolecule, by user or by type of storage identifier (e.g., epitope tagged biomolecule storage identifier, biomolecule storage identifier, epitope tag storage identifier, reactive linker storage identifier). In other embodiments, the output manager includes a printer and the identified storage identifiers are printed onto a human (paper) readable medium or as in a machine readable format (e.g., as a barcode).

In certain embodiments, the output manager communicates the storage identifiers assembled by the processing module, e.g., one or more epitope tagged biomolecule storage identifiers, biomolecule storage identifiers, epitope tag storage identifiers, reactive linker storage identifiers in an electronic format to a user, such as over a local area network or over the Internet. The electronic communication of data by the output manager may be implemented according to a convenient protocol, including but not limited to, SQL, HTML or XML documents, email or other files, or data in other forms. The data may also include Internet URL addresses so that a user may retrieve additional SQL, HTML, XML, or other documents or data from remote sources.

Systems of the present disclosure for inputting an epitope tagged biomolecule reagent request, storing a plurality of storage identifiers that correspond with the components the of the epitope tagged biomolecule reagent request, identifying one or more storage identifiers and for outputting the identified storage identifiers include a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in certain embodiments, include a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of the computer is controlled primarily by an operating system, which is executed by the central processing unit. The operating system can be stored in a system memory. In some embodiments, the operating system includes a file system. In addition to an operating system, one possible implementation of the system memory includes a variety of programming files and data files for implementing the method described below. In certain cases, the programming can contain a program, where the program can be composed of various modules, and a user interface module that permits a user to manually select or change the inputs to or the parameters used by the program. The data files can include various inputs for the program.

In certain embodiments, instructions in accordance with the method described herein can be coded onto a computer-readable medium in the form of "programming," where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programs that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

In any embodiment, data can be forwarded to a "remote location," where "remote location," means a location other than the location at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Some embodiments include implementation on a single computer, or across a network of computers, or across networks of networks of computers, for example, across a network cloud, across a local area network, on hand-held computer devices, etc. In certain embodiments, one or more of the steps described herein are implemented on a computer program(s). Such computer programs execute one or more of the steps described herein. In some embodiments, implementations of the subject method include various data structures, categories, and modifiers described herein, encoded on computer-readable medium(s) and transmissible over communications network(s).

Software, web, internet, cloud, or other storage and computer network implementations of the present invention could be accomplished with standard programming techniques to conduct the various assigning, calculating, identifying, scoring, accessing, generating or discarding steps.

Figure 5:
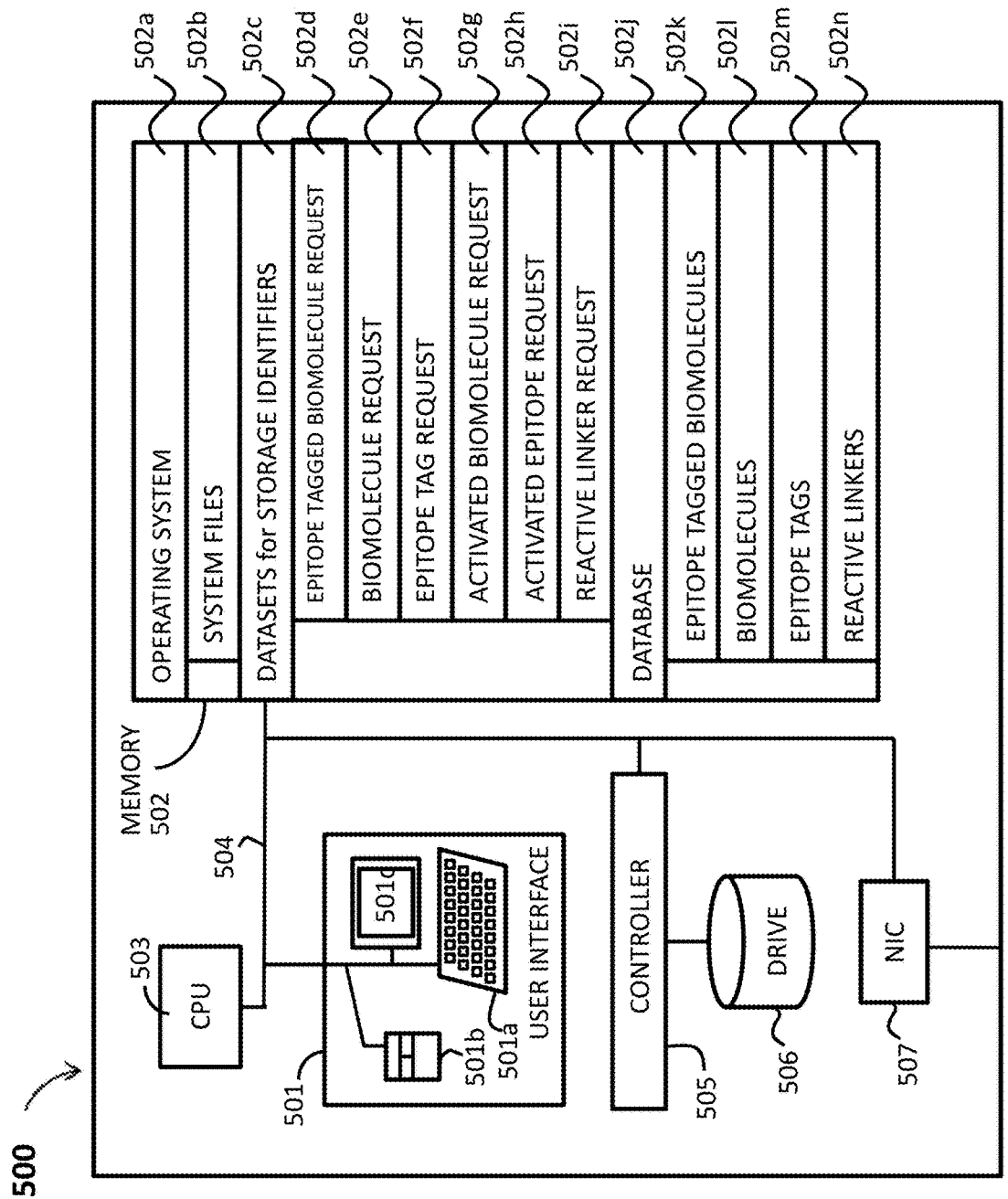
FIG. 5 depicts a computer system of the present disclosure according to certain embodiments of the invention.

FIG. 5 depicts a computer system 500 of the present disclosure according to certain embodiments. The computer system includes user interface 501 that includes a keyboard 501a, a mouse 501b and monitor 501c for inputting an epitope tagged biomolecule reagent request. User interface 501 is operatively coupled to a memory 502 that includes operating system 502a, system files 502b and datasets that include a plurality of storage identifiers that correspond to the components of the epitope tagged biomolecule reagent request: 1) epitope tagged biomolecule request 502d; 2) biomolecule request 502e; 3) epitope tag request 502f; 4) activated biomolecule request 502g; 5) activated epitope tag request 502h; and 6) reactive linker request 502i. Memory 502 also includes a database 502j that includes a searchable inventory listing of epitope tagged biomolecules 502k, biomolecules 502l, epitope tag 502m and reactive linkers 502n.

The memory and user interface are operatively coupled to a processor 503 through connection 504 that includes a storage drive 506 that is controlled by disk controller 505. As described above, the processor identifies one or more storage identifiers from the dataset that corresponds to the request received by the input manager.

To output the identified storage identifiers, systems of interest according to this embodiment include a network interface controller 507 which outputs the storage identifiers. Network interface controller 507 may be interfaced with an electronic display to visually display the identified storage identifiers or may be interfaced with a printer for presenting the identified storage identifiers onto a human (paper) readable medium or as in a machine readable format (e.g., as a barcode). In certain instances, network interface controller 507 communicates the storage identifiers in an electronic format, such as over a local area network or over the internet and may be implemented according to any electronic format, including but not limited to, SQL, HTML or XML documents, email or other files, or data in other forms.

Figure 6:
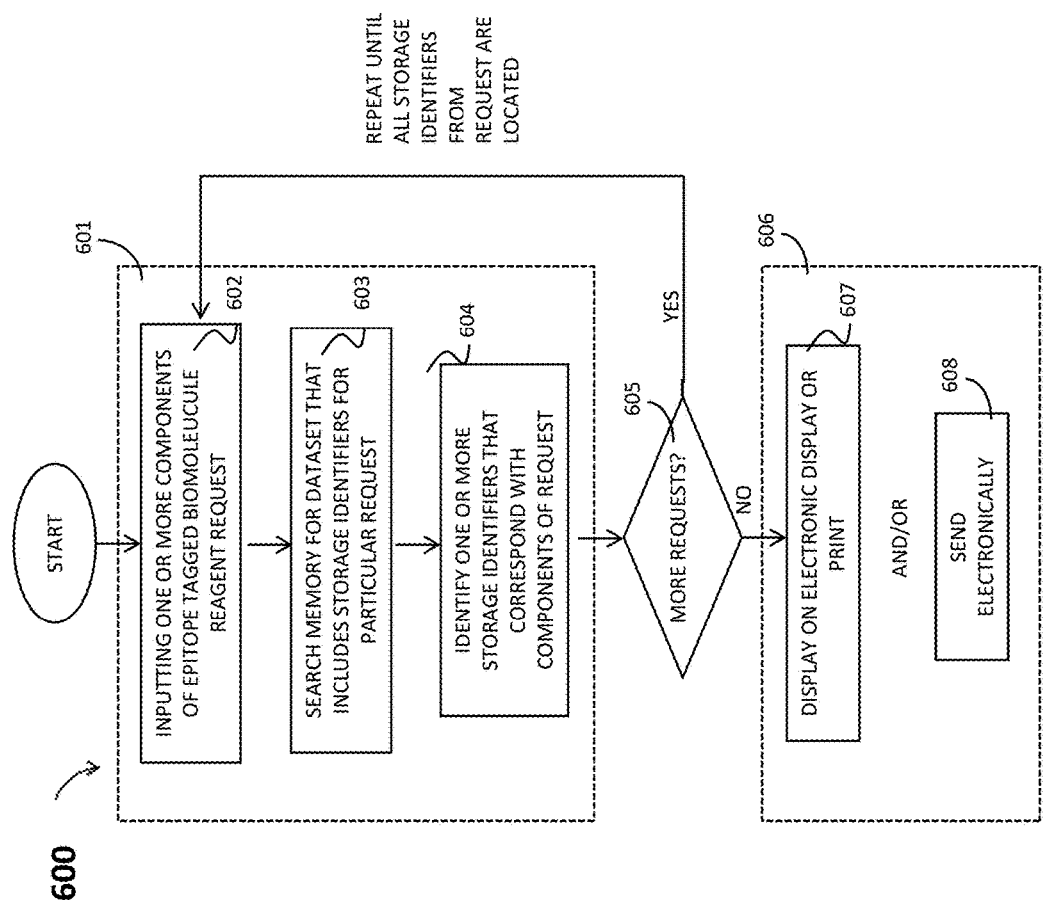
FIG. 6 illustrates a flow diagram for receiving, processing and outputting a request for an epitope tagged biomolecule reagent according to certain embodiments of the invention.

FIG. 6 illustrates a flow diagram 600 for receiving, processing and outputting a request for an epitope tagged biomolecule reagent according to certain embodiments. Receiving and processing 601 the request starts with inputting the one or more components of the epitope tagged biomolecule reagent request (602). As discussed above, the epitope tagged biomolecule reagent request may include one or more of 1) an epitope tagged biomolecule request; and 2) a biomolecule request and an epitope tag request. In some instances, the biomolecule request is an activated biomolecule request where biomolecule is coupled to a reactive linker. In other instances, the epitope tag request is an activated epitope tag request where the epitope tag is coupled to a reactive linker.

After the systems has received the epitope tagged biomolecule reagent request, a processor determines the components of the request (i.e., epitope tagged biomolecule request; or biomolecule request and epitope tag request) and the system searches (603) the memory for storage identifiers that correspond to that particular request. When the appropriate dataset is retrieved, the processing module identifies one or more storage identifiers that correspond with the components of the epitope tagged biomolecule reagent request (604). If more than one epitope tagged biomolecule reagent request is inputted by a single user, the system may repeat the above until all storage identifiers from the user's requests are located and identified by the processor (605).

Systems are configured to output (606) the identified storage identifiers once the epitope tagged biomolecule reagent request from the user has been processed. The output manager may display the storage identifiers on an electronic display or print the storage identifiers (607). The storage identifiers may also be communicated electronically (608), such as to a reagent preparatory apparatus or over the internet to a third party manufacturer.

In some embodiments, systems include a reagent preparatory apparatus for preparing the epitope tagged biomolecule reagent that corresponds to the requested epitope tagged biomolecule received by the input manager. The reagent preparatory apparatus is operatively coupled to the output manager and is configured to receive the identified storage identifiers (e.g., epitope tagged biomolecule storage identifier, biomolecule storage identifier, epitope tag storage identifier, reactive linker storage identifier) and produce the epitope tagged biomolecule reagent according to the received storage identifiers. In these embodiments, the reagent preparatory apparatus may be in communication with the output manager locally, such as through a cable or local area network or may be in a remote location and connected to the output manager through a wide-area network or through the internet. To facilitate connectivity between the reagent preparatory apparatus and the output manager, systems may include any suitable connectivity protocols, such as a cables, transmitters, relay stations, network servers, network interface cards, Ethernet modems, telephone network connections as well as satellite network connections. In certain embodiments, the reagent preparatory apparatus includes a graphical user interface where the storage identifiers from the output manager are manually inputted into an input manager operatively coupled to the graphical user interface of the reagent preparatory apparatus.

In certain embodiments, the reagent preparatory apparatus is fully automated. By "fully automated" is meant that the reagent preparatory apparatus receives the identified storage identifiers from the output manager and prepares, formulates and packages the epitope tagged biomolecule reagent with little to no human intervention or manual input into the subject systems. In certain embodiments, the subject systems are configured to prepare, purify and package the epitope tagged biomolecule reagent from an activated biomolecule and activated epitope tag without any human intervention.

The reagent preparatory apparatus includes a sampling device that provides an activated biomolecule and an activated epitope tag to a contacting apparatus. The sampling device may be any convenient device in fluid communication with each source of activated biomolecule and activated epitope tag, such as for example, a high throughput sample changer having a plurality of reagent vials containing activated biomolecules and activated epitope tags. The sampling device may also include microfluidic channels, syringes, needles, pipets, aspirators, among other sampling devices. The contacting apparatus may be any suitable apparatus which allows for an activated biomolecule to be contacted with an activated epitope tag. For example, in some embodiments, the contacting apparatus is a sample chamber (e.g., enclosed, sealed, air-tight, open, plate, etc.). In other embodiments, the contacting apparatus is a microtube. In other embodiments, the contacting apparatus is a test tube. In yet other embodiments, the contacting apparatus is a glass flask (e.g., beaker, volumetric flask, Erlenmeyer flask, etc.). In still other embodiments, the contacting apparatus is a 96-well plate. In certain embodiments, the subject systems may further include a packaging unit configured to seal the produced epitope tagged biomolecule reagent in the contacting apparatus (e.g., microtube, test tube, etc.). In other embodiments, the produced epitope tagged biomolecule reagent is first characterized and further purified, diluted, concentrated or re-formulated before sealing in a container and packaged with the packaging unit.

The contacting apparatus may further include an agitator for mixing the combined activated biomolecule and activated epitope tag. The agitator may be any convenient agitator sufficient for mixing the subject compositions, including but not limited to vortexers, sonicators, shakers (e.g., manual, mechanical, or electrically powered shakers), rockers, oscillating plates, magnetic stirrers, static mixers, rotators, blenders, mixers, tumblers, orbital shakers, bubbles, microfluidic flow, among other agitating protocols.

In some embodiments, the reagent preparatory apparatus also includes a source of activated biomolecules and activated epitope tags. The source may include a plurality of activated biomolecules and activated epitope tags. In some instances, the reagent preparatory apparatus includes a source containing 5 or more different types of activated biomolecules, such as 10 or more, such as 100 or more, such as 250 or more, such as 500 or more and including 1000 or more different types of activated biomolecules. For example, the reagent preparatory apparatus may include a source containing 5 or more different types of activated antibody probes or activated oligonucleotide probes, such as 10 or more, such as 100 or more, such as 250 or more, such as 500 or more and including 1000 or more different types of activated antibody probes or activated oligonucleotide probes.

In some embodiments, the reagent preparatory apparatus includes a source containing 5 or more different types of activated epitope tags, such as 10 or more, such as 15 or more, such as 25 or more, such as 50 or more and including 100 or more different types of activated epitope tags. For example, the reagent preparatory apparatus may include a source containing 5 or more different types of activated fluorophores, such as 10 or more, such as 15 or more, such as 25 or more, such as 50 or more and including 100 or more different types of activated epitope tags specific for different anti-species specific secondary immunoassay reagents.

The source of activated biomolecules and activated epitope tags may be any suitable reservoir that is capable of storing and providing one or more type of activated biomolecule and activated epitope tag to the contacting apparatus. In one example, the source is a single high throughput reservoir that stores a plurality of different types of activated biomolecules and activated epitope tags in separate, partitioned reagent chambers. In another example, the source of activated biomolecules and activated epitope tags is a plurality of individual vials of each activated biomolecule and each activated epitope tag. In yet another example, the source of activated biomolecules and activated epitope tags is a reservoir with pre-measured aliquots of each activated biomolecule and each activated epitope tag. For example, the reservoir may include pre-measured aliquots of each activated biomolecule and each activated epitope tag sufficient to prepare one or more epitope tagged biomolecules, such as 2 or more, such as 5 or more, such as 10 or more, such as 25 or more, such as 100 or more, such as 500 or more and including 1000 or more epitope tagged biomolecules. Depending on the particular design of reservoir containing the activated biomolecules and activated epitope tags, the reagent preparatory apparatus may further include one or more inlets for delivering the activated biomolecules and activated epitope tags to the contacting apparatus.

The reagent preparatory apparatus may also include one or more reagent purifiers. Reagent purification protocols of interest may include, but is not limited to size exclusion chromatography, ion exchange chromatography, filtration (e.g., membrane filters, size cut-off filtration), liquid-liquid extraction, passive dialysis, active dialysis, centrifugation, precipitation, among other purification protocols.

The reagent preparatory apparatus may also include a reagent analyzer. In certain embodiments, the sample analyzer may be mass cytometry, mass spectrometry (e.g., TOF mass spectrometry, inductively coupled plasma mass spectrometry), absorbance spectroscopy, fluorescence spectroscopy, volumetric analysis, conductivity analysis, nuclear magnetic resonance spectroscopy, infrared spectroscopy, UV-vis spectroscopy, colorimetry, elemental analysis, liquid chromatography-mass spectrometry or gas chromatography-mass spectrometry systems. For example, the apparatus may include analytical separation device such as a liquid chromatograph (LC), including a high performance liquid chromatograph (HPLC), fast protein liquid chromatography (FPLC) a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, the subject sample may be applied to the LC-MS system by employing a nano- or micropump in certain embodiments. Mass spectrometer systems may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multimode" ionization source). In one embodiment, the precursor ions may be made by EI, ESI or MALDI, and a selected precursor ion may be fragmented by collision or using photons to produce product ions that are subsequently analyzed. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

The reagent preparatory apparatus may also be configured to formulate the epitope tagged biomolecule reagent with one or more excipients, such as a buffer, preservative, drying agent, etc. In certain embodiments, the reagent preparatory apparatus is configured to formulate the epitope tagged biomolecule reagent with one or more buffers. Example buffers may include but are not limited to PBS (phosphate) buffer, acetate buffer, N,N-bis(2-hydroxyethyl)glycine (Bicine) buffer, 3-{[tris(hydroxymethyl)methyl]amino}propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3-[N-Tris(hydroxymethyl)methylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino}ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of buffered solutions.

The reagent preparatory apparatus may also include a packing unit for packaging the epitope tagged biomolecule reagent. In certain embodiments, the packaging unit may package the prepared epitope tagged biomolecule reagent and prepare the epitope tagged biomolecule reagent for shipping, such as by mail. In certain instances, the prepared epitope tagged biomolecule reagent is dispensed into a container and sealed. In other instances, the epitope tagged biomolecule reagent is dispensed into a container, sealed and further packaged such as in a pouch, bag, tube, vial, microtube or bottle. Where desired, the packaging may be sterile.

In certain embodiments, systems of interest include an on-demand standalone epitope tagged biomolecule reagent dispensing station configured to: 1) receive one or more requests for an epitope tagged biomolecule reagent; 2) prepare the requested epitope tagged biomolecule reagent and 3) deliver the prepared epitope tagged biomolecule reagent to the requestor (e.g., customer). For example, the standalone reagent dispensing station may be a self-vending machine that is configured to receive one or more epitope tagged biomolecule reagent requests from a customer, prepare the requested epitope tagged biomolecule and dispense the prepared epitope tagged biomolecule to the customer on demand. Depending on the number of epitope tagged biomolecule reagent requests and the amount of each epitope tagged biomolecule reagents requested, standalone reagent dispensing stations of interest may prepare and dispense the epitope tagged biomolecule to the requestor on demand in 10 seconds or more after input of the epitope tagged biomolecule request, such as in 15 seconds or more, such as in 30 seconds or more, such as in 1 minute or more, such as in 5 minutes or more, such as in 10 minutes or more, such as in 15 minutes or more, such as in 30 minutes or more and including in 60 minutes or more, such as in 1.5 hours or more, such as in 2 hours or more, such as in 2.5 hours or more, such as in 3 hours or more, such as in 4 hours or more, such as in 5 hours or more, such as in 6 hours or more, such as in 8 hours or more, such as in 10 hours or more, such as in 12 hours or more, such as in 16 hours or more, such as in 18 hours or more and including in 24 hours or more. In some instances, the standalone reagent dispensing station is configured to prepare and dispense the epitope tagged biomolecule to the requestor on demand in a duration that ranges from 5 seconds to 60 seconds, such as from 10 seconds to 50 seconds and including from 15 seconds to 45 seconds. In other instances, the standalone reagent dispensing station is configured to prepare and dispense the epitope tagged biomolecule to the requestor on demand in a duration that ranges from 1 minute to 60 minutes, such as from 2 minutes to 55 minutes, such as from 5 minutes to 50 minutes, such as from 15 minutes to 45 minutes and including from 20 minutes to 40 minutes, for example preparing and dispensing the epitope tagged biomolecule to the requestor in 30 minutes. In still other instances, the standalone reagent dispensing station is configured to prepare and dispense the epitope tagged biomolecule to the requestor on demand in a duration that ranges from 0.5 hours to 24 hours, such as from 1 hour to 20 hours, such as from 1.5 hours to 18 hours, such as from 2 hours to 16 hours, such as from 2.5 hours to 12 hours, such as from 3 hours to 10 hours, such as from 3.5 hours to 8 hours and including from 4 hours to 6 hours.

In these embodiments, the subject standalone reagent dispensing stations may include the components for receiving an epitope tagged biomolecule reagent request and preparing the requested epitope tagged biomolecule reagent, as described above. For instance, the standalone epitope tagged biomolecule reagent dispensing station may include an input module for receiving a request for an epitope tagged biomolecule; a reagent preparatory apparatus; and a dispensing module for outputting a packaged epitope tagged biomolecule. In these embodiments, the input module may include an input manager for receiving a request for an epitope tagged biomolecule, a memory for storing a dataset having a plurality of storage identifiers that correspond to the one or more components of the epitope tagged biomolecule reagent request (e.g., biomolecule, epitope, etc.), a processing module communicatively coupled to the memory and configured to identify a storage identifier from the dataset that corresponds to the components of the epitope tagged biomolecule reagent request and an output manager for providing the identified storage identifiers. The standalone station also includes, as described above, a graphical user interface as well as user input devices for communicating the epitope tagged biomolecule request to the input manager of the standalone dispensing station.

In embodiments, the output manager is communicatively coupled to the reagent preparatory apparatus in the standalone reagent dispensing station which is configured with one or more sources of biomolecules, epitope tags, reactive linkers, activated biomolecules and activated epitope tags and a contacting station for coupling an activated biomolecule and an activated epitope tags to produce the requested epitope tagged biomolecule. In certain embodiments, the standalone reagent dispensing station includes a plurality of pre-synthesized epitope tagged biomolecules and the standalone reagent dispensing station is configured to aliquot an amount of the pre-synthesized epitope tagged biomolecule reagent into a container and dispense the epitope tagged biomolecule reagent to the requestor.

The standalone epitope tagged biomolecule reagent dispensing station also includes a dispensing module that is configured to provide a packaged epitope tagged biomolecule reagent. In embodiments, the dispensing module may include a packaging epitope tagged biomolecule reagent. In certain instances, the prepared epitope tagged biomolecule reagent is dispensed into a container and sealed. In other instances, the epitope tagged biomolecule reagent is dispensed into a container, sealed and further packaged such as in a pouch, bag, tube, vial, microtube or bottle. Where desired, the packaging may be sterile.

In certain embodiments, the standalone reagent dispensing station is fully automated, where an epitope tagged biomolecule request is received and the station prepares, purifies and packages the epitope tagged biomolecule reagent with little to no human intervention or manual input into the subject systems apart from the epitope tagged biomolecule request.

Methods for Preparing an Epitope Tagged Biomolecule Reagent

Aspects of the present disclosure also include methods for preparing an epitope tagged biomolecule reagent. Methods according to certain embodiments include receiving a request for an epitope tagged biomolecule reagent and preparing an epitope tagged biomolecule. In other embodiments, methods include receiving a request for an epitope tagged biomolecule reagent with one or more input managers as described above, identifying a storage identifier that corresponds with the epitope tagged biomolecule reagent request; outputting the one or more identified storage identifiers and preparing the epitope tagged biomolecule from the identified storage identifiers.

As discussed above, the epitope tagged biomolecule reagent is a biological macromolecule that is coupled (e.g., covalently bonded) to an epitope tag. In some embodiments, methods include preparing a polypeptide coupled to an epitope tag, a nucleic acid coupled to an epitope tag, a polysaccharide coupled to an epitope tag, or a combination thereof. In one example, the biomolecule is an oligonucleotide, truncated or full-length DNA or RNA. In another example, the biomolecule is a polypeptide, protein, enzyme or antibody. In certain instances, the biomolecule is a biological probe having a specific binding domain sufficient to bind an analyte of interest. Specific binding domains of interest include, but are not limited to, antibody binding agents, proteins, peptides, haptens, nucleic acids, etc. As reviewed in greater detail above, the term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments, as well as molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

As reviewed above, epitope tags are molecular entities that include a desired discrete site, i.e., epitope, to which a secondary antibody of an indirect immunoassay specifically binds. The molecular entity (i.e., epitope tag) that includes the epitope may be any type of molecule, where molecular entities of interest includes any of the biomolecules described above, e.g., peptides, saccharides, nucleic acids, small molecules, etc. In certain embodiments, the epitope tag is a polypeptide that includes a species-specific epitope such that, upon binding to a biomolecule in accordance with the invention, confers a species-specific epitope on the biomolecule. In such instances, the epitope tag may be a polypeptide ranging in size, ranging in some instances from 1 to 100,000, such as 5 to 1,000, including 5 to 100, e.g., 5 to 30 and including 5 to 20 residues in length. The species-specific epitope is, in some instances, an epitope found in antibodies to a particular antigen raised in a given species, such that it is an epitope found in antibodies raised in a given species to particular antibody. The species may vary, where examples of species include, but are not limited to, mouse, goat, rabbit, rat, horse, chicken, human, etc. The species-specific epitope may also be an epitope from a particular antibody isotype, e.g., IgG, IgA, IgM, IgD or IgE. The epitope tag that is bonded to a biomolecule reagent may be one that is chosen based on a desired secondary antibody, which secondary antibody may vary widely. Examples of secondary antibodies for which a given epitope tag may be selected for a given epitope tagged biomolecule reagent include, but are not limited to, anti-mouse, anti-goat, anti-rabbit, anti-rat, anti-horse, anti-chicken, anti-human, etc., secondary antibodies, where the secondary antibodies may be ones that bind to a particular isotype, e.g., IgG, IgA, IgM, IgD or IgE.

Methods include receiving a request for an epitope tagged biomolecule reagent. In embodiments of the present disclosure, the epitope tagged biomolecule reagent request includes one or more of: 1) an epitope tagged biomolecule request; and 2) a biomolecule request and an epitope request. In some instances, the biomolecule request is an activated biomolecule request where biomolecule is coupled to a reactive linker. In other instances, the epitope/epitope tag request is an activated epitope tag request where the epitope tag is coupled to a reactive linker. The epitope tagged biomolecule reagent request may be received by any convenient communication protocol including, but not limited to, receiving the epitope tagged biomolecule reagent request over the telephone, by facsimile, electronic mail or postal mail. In certain embodiments, the epitope tagged biomolecule reagent request is communicated by inputting the epitope tagged biomolecule reagent request into a graphical user interface on a computer, such as through an internet website.

One or more epitope tagged biomolecule reagent requests may be received (simultaneously or sequentially), such as receiving 2 or more epitope tagged biomolecule reagent requests, such as 5 or more, such as 10 or more and including receiving 25 or more epitope tagged biomolecule reagent requests. Where the request for an epitope tagged biomolecule reagent includes only a single component and is an epitope tagged biomolecule request, methods may include receiving 2 or more epitope tagged biomolecule requests, such as 5 or more, such as 10 or more and including 25 or more epitope tagged biomolecule requests. Where the epitope tagged biomolecule reagent request includes two components, such as a biomolecule request and an epitope/epitope tag request, methods may include receiving 2 or more biomolecule requests, such as 5 or more, such as 10 or more and including 25 or more biomolecule requests and 2 or more epitope tag requests, such as 5 or more, such as 10 or more and including 25 or more epitope tag requests. In some instances, methods including receiving an epitope tagged biomolecule reagent request that includes a single biomolecule request and single epitope tag request. In other instances, methods include receiving an epitope tagged biomolecule reagent request that includes a single biomolecule request and a plurality of different epitope tag requests. In yet other instances, the methods include receiving an epitope tagged biomolecule reagent request that includes a plurality of different biomolecule requests and a single epitope tag request. In still other instances, methods include receiving an epitope tagged biomolecule reagent request that includes a plurality of different biomolecule requests and a plurality of different epitope tag requests.

The epitope tagged biomolecule reagent requests may be received from a single user or a plurality of users, such as from 2 or more users, such as from 5 or more users, such as from 10 or more users, such as from 25 or more users and including receiving epitope tagged biomolecule requests from 100 or more users.

In certain embodiments, methods include receiving a request for an epitope tagged biomolecule reagent and inputting the request into a graphical user interface of an input manager (as described above) entered through. In other embodiments, the user making the epitope tagged biomolecule reagent request inputs the request directly into the graphical user interface. The epitope tagged biomolecule request, in these embodiments, may be entered into the graphical user interface and communicated to the input manager as a string of one or more characters (e.g., alphanumeric characters), symbols, images or other graphical representation(s) of the epitope tagged biomolecule. In some instances, the request is a "shorthand" designation or other suitable identifier of the epitope tagged biomolecule, biomolecule, epitope tag, activated biomolecule, activated epitope tag or reactive linker. For example, the request may include biomolecule name, epitope name or species, ascension number, sequence identification number, abbreviated probe sequence, chemical structure or Chemical Abstracts Service (CAS) registry number.

As described above, after the epitope tagged biomolecule request is received by the input manager, a processing module of the subject systems identifies one or more storage identifiers from a dataset stored in memory that corresponds to the components of the received epitope tagged biomolecule reagent request (e.g., an epitope tagged biomolecule storage identifier, a biomolecule storage identifier, an epitope tag storage identifier, a reactive linker storage identifier, etc.) The storage identifiers that correspond to each component of the received epitope tagged biomolecule reagent request is outputted by an output manager. In some instances, each epitope tagged biomolecule storage identifier is displayed on a monitor. In other instances, the storage identifiers is outputted by printing in a machine (e.g., as a barcode) or human readable format. Where the epitope tagged biomolecule reagent is prepared by a computer controlled reagent preparatory apparatus (as described in greater detail below), the output manager is operatively coupled to the reagent preparatory apparatus and each storage identifier may electronically communicated to the reagent preparatory apparatus, such as through an internet protocol, including but not limited to SQL, HTML or XML documents, email or other files, or data in other forms.

Depending on the number of epitope tagged biomolecule requests received, one or more storage identifiers may be simultaneously outputted by the output manager, such as 2 or more, such as 3 or more, such as 3 or more, such as 5 or more, such as 10 or more, such as 25 or more, such as 100 or more and including outputting 500 or more storage identifiers. Each set of outputted storage identifiers may correspond with the epitope tagged biomolecule requests from a single user or from a plurality of users.

In certain embodiments, the output manager organizes (e.g., groups together) storage identifiers based on a predetermined criteria before displaying or printing the storage identifiers. In one example, the output manager groups together all of the storage identifiers from a particular user. In another example, the output manager groups together all of the same epitope tagged biomolecule storage identifiers. In yet another example, the output manager organizes the storage identifiers based on name or type of biomolecule (e.g., antibody, oligonucleotide). In still another example, the output manager organizes the storage identifiers based on the name or type of epitope (e.g., rabbit, mouse, human, etc.).

In some embodiments, methods include preparing an epitope tagged biomolecule reagent according to the received request and/or the outputted storage identifiers. In some embodiments, preparing the epitope tagged biomolecule reagent includes selecting an activated biomolecule and an activated epitope tag from a storage having a plurality of activated biomolecules and a plurality of activated epitope tags. Each epitope tagged biomolecule reagent may be prepared manually by one or more individuals, such as in a laboratory or may be prepared with a computer-controlled reagent preparatory apparatus (e.g., a high throughput preparatory system) as described above. In some instances, where the outputted storage identifier is an epitope tagged biomolecule storage identifier, methods include retrieving the epitope tagged biomolecule from a storage that corresponds to the outputted epitope tagged biomolecule storage identifier. In these instances, methods may further include purifying the epitope tagged biomolecule from the storage or adding one or more additional reagents (e.g., buffers, antioxidants, etc.) as desired. In other instances, the retrieved epitope tagged biomolecule may be packaged and shipped to the user without further purification or additions to the composition.

In other embodiments, the epitope tagged biomolecule is prepared by contacting an activated biomolecule that corresponds with the outputted biomolecule storage identifier with an activated epitope tag that corresponds with the outputted epitope tag storage identifier. Any convenient reaction protocol may be employed to mix the activated biomolecule with the activated epitope tag, so long as the reaction is sufficient to form a covalent bond between the reactive linker of the activated biomolecule and the reactive linker of the activated epitope tag. Mixing, in certain embodiments, may include stirring the mixture with a magnetic stir bar or manually stirring the mixture as well as vortexing of agitating the mixture either manually (i.e., by hand) or mechanically (i.e., by a mechanically or electrically powered shaking device). The activated biomolecule and activated epitope tag are contacted for a duration sufficient to couple the activated biomolecule to the activated epitope tag, such as for 1 minute or longer, such as for 5 minutes or longer, such as for 10 minutes or longer and including for 30 minutes or longer.

As discussed above, the activated biomolecule and activated epitope tag each include a reactive linker which when carried out under appropriate conditions, react together to form chemical linkage, such as for example, an ionic bond (charge-charge interaction), a non-covalent bond (e.g., dipole-dipole or charge-dipole) or a covalent bond. In some embodiments, the reactive linker or moiety of the activated biomolecule reacts with the reactive linker or moiety of the activated epitope tag to produce an ionic bond. In other embodiments, the reactive linker or moiety of the activated biomolecule reacts with the reactive linker or moiety of the activated eptiope to produce a non-covalent bond. In yet other embodiments, the reactive linker or moiety of the activated biomolecule reacts with the reactive linker or moiety of the activated epitope tag to produce a covalent bond. In certain embodiments, the reactive linker of the activated biomolecule and the reactive linker of the activated epitope tag react to produce a covalent bond. Any convenient protocol for forming a covalent bond between the reactive linker of the activated biomolecule and the reactive linker of the activated epitope tag may be employed, including but not limited to addition reactions, elimination reactions, substitution reactions, pericyclic reactions, photochemical reactions, redox reactions, radical reactions, reactions through a carbene intermediate, metathesis reaction, among other types of bond-forming reactions. In some embodiments, the activated biomolecule may be conjugated to the activated epitope tag through reactive linking chemistry such as where reactive linker pairs include, but is not limited to: maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate—periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[β-Maleimidopropionic acid]hydrazide.TFA)/thiol; azide/triarylphosphine; nitrone/cyclooctyne; azide/tetrazine and formylbenzamide/hydrazino-nicotinamide.

After contacting the activated biomolecule and activated epitope tag for a duration sufficient to form a chemical linkage (e.g., covalent bond) between each respective reactive linker, the epitope tagged biomolecule may be further purified, such as by microextraction, gel electrophoresis, liquid-liquid extraction, centrifugation, precipitation, passive or active dialysis, or solid phase chromatography, including but not limited to ion exchange chromatography, liquid chromatography employing a reverse phase stationary column, size exclusion chromatography, high performance liquid chromatography and preparatory thin layer chromatography, ultrafiltration (membrane filters with size cut offs), among other purification protocols.

Methods may also include analysis of the prepared epitope tagged biomolecule reagent. By analyzed is meant characterizing the chemical composition of the epitope tagged biomolecule reagent, including but not limited to the amount and types of compounds in the prepared reagent composition as well as any impurities present. Analysis of the prepared epitope tagged biomolecule reagent may be conducted using any convenient protocol, such as for example by physical measurements (e.g., mass analysis, density analysis, volumetric analysis, etc.) mass spectrometry (e.g., TOF mass spectrometry, inductively coupled plasma mass spectrometry), mass cytometry, absorbance spectroscopy, fluorescence spectroscopy, conductivity analysis, infrared spectroscopy, UV-vis spectroscopy, colorimetry, elemental analysis and nuclear magnetic resonance spectroscopy. In some instances, analysis of the epitope tagged biomolecule is conducted by mass spectrometry. In some instances, analysis of the epitope tagged biomolecule is conducted by fluorescence spectroscopy. In some instances, analysis of the epitope tagged biomolecule is conducted by gas chromatography. In some instances, analysis of the epitope tagged biomolecule is conducted by liquid chromatography. In some instances, analysis of the epitope tagged biomolecule is conducted by elemental analysis. In certain embodiments, analysis of the epitope tagged biomolecule reagent is conducted by gas chromatography-mass spectrometry. In other embodiments, analysis of the epitope tagged biomolecule reagent is conducted by liquid chromatography-mass spectrometry. For example, the apparatus may include analytical separation device such as a liquid chromatograph (LC), including a high performance liquid chromatograph (HPLC), fast protein liquid chromatography (FPLC) a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, the subject sample may be applied to the LC-MS system by employing a nano- or micropump in certain embodiments. Mass spectrometer systems may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multimode" ionization source). In one embodiment, the precursor ions may be made by EI, ESI or MALDI, and a selected precursor ion may be fragmented by collision or using photons to produce product ions that are subsequently analyzed. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

After preparation (as well as purification and analysis, where desired) of the epitope tagged biomolecule reagent, each prepared epitope tagged biomolecule reagent may be loaded into a container for packaging and delivery in accordance with the epitope tagged biomolecule request (i.e., transported to the user originating the epitope tagged biomolecule request). In certain embodiments, the epitope tagged biomolecule reagent is prepared and delivered to the user in the container used to contact the activated biomolecule with the activated epitope tag. For example, the epitope tagged biomolecule reagent may be packaged and delivered in the microtube used to contact the activated biomolecule with the activated epitope tag. Methods may also include delivering the packaged epitope tagged biomolecule reagent to the requestor, such as by mail.

The prepared epitope tagged biomolecule reagent may be packaged with other components, such as for using or storing the epitope tagged biomolecule reagent, including but not limited to one or more secondary immunoassay reagents, e.g., where a secondary immunoassay reagent may specifically bind to the epitope of the epitope tagged biomolecule reagent and may or may not be labeled with a detectable label (which label may be directly or indirectly detectable), buffers, syringes, needles, micropipets, glass slides, desiccants, etc. In some instances, the secondary immunoassay reagent is a labeled biomolecule reagent that is obtained using a system/methodology as described in PCT application serial no. US2016/050234 filed on Sep. 2, 2016, the disclosure of which is herein incorporated by reference. In addition, the packaged epitope tagged biomolecule reagent may further include instructions for storing and using the epitope tagged biomolecule reagent. The instructions may be recorded on a suitable recording medium, such as printed on paper or plastic, etc. The instructions may be present as a package insert, such as in the labeling of the container. In other embodiments, the instructions may be present as electronic storage data file present on a suitable computer readable storage medium, e.g. CD-ROM, SD card, USB drive etc. In yet other embodiments, the actual instructions are not present in the package, but means for obtaining the instructions from a remote source, e.g. via the internet, are provided. An example of this embodiment is a paper or plastic insert having a web address where the instructions can be viewed and/or from which the instructions can be downloaded.

Methods for Requesting and Receiving an Epitope Tagged Biomolecule Reagent

Aspects of the present disclosure also include methods for requesting and receiving an epitope tagged biomolecule reagent. Methods according to certain embodiments include communicating a request for an epitope tagged biomolecule reagent, the epitope tagged biomolecule request including one or more of: 1) an epitope tagged biomolecule request; and 2) a biomolecule request and an epitope/epitope tag request and receiving an epitope tagged biomolecule reagent that includes a biomolecule bonding to an epitope tag, such as covalently bonded to an epitope tag. In practicing the subject methods, the epitope tagged biomolecule request may be communicated by any convenient communication protocol including, but not limited to, communicating the epitope tagged biomolecule request over the telephone, by facsimile, electronic mail or postal mail. In certain embodiments, the epitope tagged biomolecule request is communicated by inputting the epitope tagged biomolecule reagent request into a graphical user interface on a computer, such as on an internet website.

One or more epitope tagged biomolecule reagent requests may be communicated, such as communicating 2 or more epitope tagged biomolecule reagent requests, such as 5 or more, such as 10 or more and including communicating 25 or more epitope tagged biomolecule reagent requests. In some embodiments, methods include communicating an epitope tagged biomolecule reagent request that includes a single biomolecule request and a single epitope tag request. In other embodiments, the epitope tagged biomolecule reagent request includes a single biomolecule request and a plurality of epitope tag requests. In yet other embodiments, the epitope tagged biomolecule reagent request includes a plurality of biomolecule requests and a single epitope tag request. In still other embodiments, the epitope tagged biomolecule request includes a plurality of biomolecule requests and a plurality of epitope tag requests. In certain embodiments, the epitope tagged biomolecule reagent request includes one or more epitope tagged biomolecule requests.

In certain embodiments, the epitope tagged biomolecule reagent request is communicated by inputting the request on a graphical user interface, such as on an internet website. The graphical user interface may display all or part of a database (e.g., catalog) of epitope tagged biomolecules, activated biomolecules, biomolecules, activated epitope tags, epitope tags and reactive linkers. Each category from the database may be displayed as a list, drop-down menu or other configuration. The epitope tagged biomolecule reagent request may be entered by inputting information or data associated with the biomolecule and the epitope tag into appropriate text fields or by selecting check boxes or selecting one or more items from a drop-down menu, or by using a combination thereof.

In one example, an epitope tagged biomolecule reagent request is inputted into the graphical user interface by selecting an epitope tagged biomolecule from a drop-down menu. In another example, an epitope tagged biomolecule reagent request is inputted into the graphical user interface by selecting one or more biomolecules from a first drop-down menu and one or more epitope tags from a second drop-down menu. In yet another example, an epitope tagged biomolecule reagent request is inputted into the graphical user interface by selecting one or more biomolecules from a first drop-down menu, one or more epitope tags from a second drop-down menu and one or more reactive linkers from a third drop-down menu.

To input an epitope tagged biomolecule reagent request, information or data associated with a particular epitope tagged biomolecule, biomolecule or epitope tag is entered onto the graphical user interface. The information or data entered may be a string of one or more characters (e.g., alphanumeric characters), symbols, images or other graphical representation(s) of the epitope tagged biomolecule. In some instances, a "shorthand" designation or other suitable identifier of the epitope tagged biomolecule, biomolecule, epitope tag, activated biomolecule, activated epitope tag or reactive linker are entered. For example, biomolecule name, epitope name, ascension number, sequence identification number, abbreviated probe sequence, epitope species, epitope species and type, chemical structure or Chemical Abstracts Service (CAS) registry number may be entered.

In some embodiments, the epitope tagged biomolecule reagent includes a polypeptide and the request may include information such as polypeptide name, protein name, enzyme name, antibody name or the name of protein, enzyme or antibody fragments thereof, polypeptides derived from specific biological fluids (e.g., blood, mucus, lymphatic fluid, synovial fluid, cerebrospinal fluid, saliva, bronchoalveolar lavage, amniotic fluid, amniotic cord blood, urine, vaginal fluid and semen), polypeptides derived from specific species (e.g., mouse monoclonal antibodies) as well as amino acid sequence identification number. In certain embodiments, the epitope tagged biomolecule reagent includes a biological probe and the request includes information or data associated with a specific binding domain.

In other embodiments, the epitope tagged biomolecule reagent includes a nucleic acid and the request may include information such as oligonucleotide name, oligonucleotides identified by gene name, oligonucleotides identified by accession number, oligonucleotides of genes from specific species (e.g., mouse, human), oligonucleotides of genes associated with specific tissues (e.g., liver, brain, cardiac), oligonucleotides of genes associate with specific physiological functions (e.g., apoptosis, stress response), oligonucleotides of genes associated with specific disease states (e.g., cancer, cardiovascular disease) as well as nucleotide sequence identification number.

In certain embodiments, methods for requesting an epitope tagged biomolecule further include completing a questionnaire or survey related to the epitope tagged biomolecule request. In these embodiments, the requestor of the epitope tagged biomolecule is prompted with a series of questions, or in the form of a questionnaire or survey related to the epitope tagged biomolecule request. For example, the questionnaire or survey may include one question related to the epitope tagged biomolecule request, such as 2 or more questions, such as 3 or more questions, such as 4 or more questions and including 5 or more questions related to the epitope tagged biomolecule request. The content of questionnaire or survey may vary depending on the information that is desired. For instance, questions in the questionnaire or survey may include, but are not limited to, requests to provide the contents of a requestor's reagent inventory, the types of experiments being conducted with the epitope tagged biomolecule as well as the timing of the use of the epitope tagged biomolecule reagent. The questionnaire may also include one or more open text fields for inputting. For example, the questionnaire may be an open text feedback form.

In some embodiments, methods include prompting the requestor to complete the series of questions or survey before the epitope tagged biomolecule request is communicated (e.g., inputted into the graphical user interface). In other embodiments, methods include prompting the requestor to complete the series of questions or survey after the epitope tagged biomolecule request is completed. In still other embodiments, the requestor may be prompted with questions related to the epitope tagged biomolecule request concurrently with communicating the epitope tagged biomolecule request. For instance, methods may include prompting the requestor with a question about the specific use (e.g., experiments being conducted) of the epitope tagged biomolecule when communicating the epitope tagged biomolecule request.

As described above, the completed series of questions or survey may be used by the design platform to provide a recommendation for one or more epitope tagged biomolecule, biomolecule, activated biomolecule, epitope tag, activated epitope tag or reactive linker. For example, the answers to the questions or survey may be used by the design platform to recommend an epitope tagged biomolecule, biomolecule, activated biomolecule, eptiope, activated eptiope or reactive linker that is best suited for use with a particular analytical instrument (e.g., flow cytometer, fluorescence spectrometer) or that is best suited for the intended application of the epitope tagged biomolecule. The design platform, in certain embodiments, is configured to use the answers to the completed series of questions or surveys to provide a recommendation for an epitope tagged biomolecule, biomolecule, activated biomolecule, epitope tag, activated epitope tag or reactive linker based on the target density (e.g., antigen density on a cell)

The answers to the series of questions or survey may be communicated using the same or different protocol as used to communicate the epitope tagged biomolecule request (e.g., telephone, facsimile, email, graphical user interface at a standalone station, graphical user interface through the internet). For example, where the epitope tagged biomolecule is request is communicated through a graphical user interface through the internet, answers to the series of questions may also be inputted through the graphical user interface, such as with drop down menus or text fields.

Methods according to embodiments of the present disclosure also include receiving the epitope tagged biomolecule reagent. The epitope tagged biomolecule reagent may be received in a container and may be packaged with one or more ancillary components, such as for using or storing the subject composition. In certain embodiments, the epitope tagged biomolecule reagent is received with secondary antibodies, buffers, syringes, needles, micropipets, glass slides, desiccants, etc. The packaged epitope tagged biomolecule reagent may also be received with instructions for storing and using the epitope tagged biomolecule reagent, such as instructions printed on paper, plastic or on a computer readable medium (e.g., CD-ROM, SD-card, USB drive) or as an insert providing instructions for retrieving instructions for storing and using the subject compositions from a remote source, such as on the internet.

In some instances, methods may further include requesting a labeled secondary antibody for use a secondary immunoassay reagent with the epitope tagged biomolecule reagent. In such instances, the methods may include requesting such a secondary immunoassay reagent using the using a system/methodology as described in PCT application serial no. US2016/050234 filed on Sep. 2, 2016, the disclosure of which is herein incorporated by reference.

Storage Containing a Plurality of Activated Biomolecules and a Plurality of Activated Epitope Tags Aspects of the disclosure also include a storage containing a plurality of activated biomolecules and a plurality of activated epitope tags. As discussed in detail above, the subject epitope tagged biomolecule reagents are prepared by contacting an activated biomolecule with an activated epitope tag. In some embodiments, the activated biomolecules in the storage are polypeptides, nucleic acids, polypeptides or a combination thereof that are coupled to a reactive linker. In certain instances, the activated biomolecules in the storage are biological probes coupled to a reactive linker where the probe includes a specific binding domain for an analyte of interest, such as antibody binding agents, proteins, peptides, haptens, nucleic acids, etc. Activated epitope tags are epitope compounds that, as described above, are specifically bound by a secondary immunoassay reagent.

In embodiments, the activated biomolecules and activated epitopes for preparing the epitope tagged biomolecule reagent in accordance with the epitope tagged biomolecule reagent request are obtained from the storage. The storage may have 10 or more different activated biomolecules, such as 25 or more, such as 50 or more, such as 100 or more, such as 250 or more, such as 500 or more and including 1000 or more activated biomolecules. In one example, the storage includes 10 or more different activated oligonucleotides, such as 25 or more, such as 50 or more, such as 100 or more, such as 250 or more, such as 500 or more and including 1000 or more activated oligonucleotides. In another example the storage includes 10 or more different activated polypeptides, such as 25 or more, such as 50 or more, such as 100 or more, such as 250 or more, such as 500 or more and including 1000 or more activated polypeptides. The storage may also include 10 or more different activated epitope tags, such as 15 or more, such as 20 or more, such as 30 or more, such as 40 or more and including 50 or more different activated epitope tags.

Each of the plurality of activated biomolecules and activated epitope tags may be present in the storage in any suitable container capable of storing and providing the activated biomolecule or activated epitope tag when desired. In some embodiments, the plurality of different activated biomolecules and plurality of different activated epitope tags are stored in a single reservoir partitioned into separate reagent chambers. In other embodiments, each of the plurality of different activated biomolecules and plurality of different activated epitope tags are stored in individual containers (e.g., bottles, jugs, etc.) In yet other embodiments, each of the plurality of different activated biomolecules and plurality of different activated epitope tags are stored in a plurality of vials, where each vial includes pre-measured aliquots of each activated biomolecule and each activated epitope tag. Each container in the storage may also include a label identifying the components of the activated biomolecule or activated epitope tag (e.g., name, structure, CAS registry number, ascension number, probe sequence, species, isotype, etc. of the biomolecule, epitope tag and reactive linker). The label may also include one or more machine readable components such as a Quick Response (QR) code or a bar code.

In some embodiments, the storage also includes a database of available activated biomolecules and activated epitope tags. The database may be a printed catalog in paper or electronic form or may be a searchable electronic database, such as searchable by keyword, chemistry structure, ascension number, monomer sequence (e.g., amino acid or nucleotide sequence) or by CAS chemical registry number.

Utility

The subject systems and methods find use in preparing complex biological reagents (e.g., biological macromolecules coupled to epitope tags)—a process that is generally time consuming, financially inefficient and extraordinarily labor intensive when conducted on a large scale. The present disclosure provides a fast, efficient and highly scalable process for delivering high quality and performance specific products across a wide range of biomolecule and epitope portfolios.

The systems and methods described herein also provide a unique and new way to request and provide customized biological reagents. In addition, being able to choose pre-synthesized reagents from an extensive database (e.g., an online database), the subject systems and methods provide for user customization, where the user can create any desired epitope tagged biomolecule on-demand. By simply choosing a biological macromolecule and an epitope tag on an easy-to-use graphical interface, a user can request any epitope tagged biomolecule, which are used in a variety of different research applications and in medical diagnosis.

The present disclosure also provides access to large portfolios of complex biological reagents that are not possible when prepared by small scale synthesis. The subject systems and methods are scalable facilitating the preparation, on-demand, of thousands of different combinations of biomolecules and epitope tags. In certain embodiments, the subject systems provide fully automated protocols so that the preparation of customized epitope tagged biomolecule probes requires little, if any human input.

The present disclosure also finds use in applications where cell analysis from a biological sample may be desired for research, laboratory testing or for use in therapy. In some embodiments, the subject methods and systems may facilitate analysis of cells obtained from fluidic or tissue samples such as specimens for diseases such as cancer. Methods and systems of the present disclosure also allow for analyzing cells from a biological sample (e.g., organ, tissue, tissue fragment, fluid) with enhanced efficiency and low cost as compared to using probe compositions synthesized de novo.

Notwithstanding the appended clauses, the disclosure set forth herein is also defined by the following clauses:

1. A system for use in preparing an epitope tagged biomolecule reagent, the system comprising:

an input manager for receiving a request for an epitope tagged biomolecule reagent;

a memory for storing a dataset comprising a plurality of epitope tagged biomolecule storage identifiers;

a processing module communicatively coupled to the memory and configured to identify one or more epitope tagged biomolecule storage identifiers from the dataset that corresponds to the components of the epitope tagged biomolecule reagent request;

an output manager for providing the identified epitope tagged biomolecule storage identifiers.

2. The system of clause 1, wherein the request for an epitope tagged biomolecule reagent comprises a biomolecule request and an epitope tag request.

3. The system of clause 2, wherein the memory comprises a first dataset comprising a plurality of biomolecule storage identifiers for a plurality of activated biomolecules and a second dataset comprising a plurality of epitope tag storage identifiers for a plurality of activated epitope tags.

4. The system of any one of clauses 1 to 3, wherein the output manager is operatively coupled to a communication component configured to display the identified epitope tagged biomolecule storage identifiers.

5. The system of clause 4, wherein the communication component is an electronic display.

6. The system of clause 4, wherein the communication component is a printer.

7. The system of any one of clauses 1 to 6, wherein the input manager is operatively coupled to a graphical user interface.

8. The system of any one of clauses 1 to 7, wherein the graphical user interface comprises an internet website menu interface.

9. The system of any one of clauses 1 to 8, wherein the input manager is configured to receive a plurality of epitope tagged biomolecule requests.

10. The system of clause 9, wherein the input manager is configured to simultaneously receive a plurality of biomolecule requests and epitope tag requests.

11. The system of clause 9, wherein the input manager is configured to receive a plurality of biomolecule requests and epitope tag requests from the same user.

12. The system of clause 9, wherein the input manager is configured to receive a plurality of biomolecule requests and epitope tag requests from a plurality of users.

13. The system of any one of clauses 1 to 12, wherein the memory comprises an algorithm for providing a recommendation for an alternative biomolecule when a biomolecule storage identifier that corresponds to the biomolecule request is not available.

14. The system of any one of clauses 1 to 13, wherein the memory comprises an algorithm for providing a recommendation for an alternative epitope tag when an epitope tag storage identifier that corresponds to the epitope tag request is not available.

15. The system of any one of clauses 1 to 14, further comprising a reagent preparatory apparatus for preparing the epitope tagged biomolecule reagent, wherein the reagent preparatory apparatus is operatively coupled to the output manager and is configured to:
  receive the identified biomolecule storage identifier and epitope tag storage identifier; and
  produce an epitope tagged biomolecule reagent corresponding to the received biomolecule storage identifier and the epitope tag storage identifier.

16. The system of clause 15, wherein the reagent preparatory apparatus comprises a sampling device configured to provide an activated biomolecule and an activated epitope tag to a contacting apparatus.

17. The system of clause 16, further comprising a contacting apparatus configured for contacting the activated biomolecule with the activated epitope tag to produce the epitope tagged biomolecule reagent.

18. The system of any one of clauses 16 to 17, further comprising an epitope tagged biomolecule reagent analyzer.

19. The system of clause 18, wherein the analyzer comprises a purification component for purifying the epitope tagged biomolecule reagent.

20. The system of clause 19, wherein the purification component comprises liquid chromatography.

21. The system of any one of clauses 16 to 20, further comprising a solvent chamber configured to provide one or more solvents to the contacting apparatus.

22. The system of any one of clauses 16 to 21, wherein the contacting apparatus is a microtube.

23. The system of any one of clauses 15 to 22, wherein the system comprises a reagent packaging unit configured to seal the produced epitope tagged biomolecule reagent in the container.

24. The system of any one of clauses 1 to 23, wherein the biomolecule is a compound selected from the group consisting of a polypeptide, a nucleic acid and a polysaccharide.

25. The system of clause 24, wherein the nucleic acid is an oligonucleotide, DNA or RNA.

26. The system of clause 25, wherein the biomolecule is an oligonucleotide.

27. The system of clause 24, wherein the polypeptide is a protein, enzyme or antibody.

28. The system of clause 27, wherein the biomolecule is an antibody.

29. The system of any one of clauses 1 to 28, wherein the epitope tag is polypeptide ranging in length from 1 to 100,000 amino acid residues.

30. The system of any one of clauses 1 to 29, wherein the memory comprises 25 or more biomolecule storage identifiers.

31. The system of clause 30, wherein the memory comprises 25 or more antibody storage identifiers.

32. The system of any one of clauses 1 to 31, wherein the memory comprises 10 or more epitope tag storage identifiers.

33. The system of clause 32, wherein the memory comprises 25 or more epitope tag storage identifiers.

34. The system of any one of clauses 1 to 33, wherein activated biomolecule and activated epitope tag each independently comprise a covalently coupled reactive linker.

35. A method comprising:
  communicating a request for an epitope tagged biomolecule reagent, the request comprising one or more of:
    an epitope tagged biomolecule request; and
    a biomolecule request and an epitope tag request; and
  receiving one or more epitope tagged biomolecule reagents, each epitope tagged biomolecule reagent comprising a biomolecule covalently coupled to an epitope tag through a linker.

36. The method of clause 35, further comprising selecting an epitope tagged biomolecule reagent from a first dataset comprising a plurality of epitope tagged biomolecule storage identifiers.

37. The method of any one of clauses 35 to 36, further comprising selecting:
  a biomolecule from a second dataset comprising a plurality of biomolecule storage identifiers; and
  an epitope tag from a third dataset comprising a plurality of epitope tag storage identifiers.

38. The method of any one of clauses 35 to 37, wherein communicating the request comprises inputting the epitope tagged biomolecule reagent request into a graphical user interface operatively coupled to an input manager of a system configured to receive the epitope tagged biomolecule reagent request.

39. The method of clause 38, wherein the graphical user interface comprises an internet website menu interface.

40. The method of any one of clauses 35 to 39, wherein communicating the epitope tagged biomolecule reagent request comprises providing the epitope tagged biomolecule reagent request by mail, electronic mail or over the telephone.

41. The method of any one of clauses 35 to 40, wherein the method comprises communicating a request for a plurality of epitope tagged biomolecule reagents.

42. The method of clause 41, wherein the request for a plurality of epitope tagged biomolecule reagents comprises a plurality of biomolecule requests and a plurality of epitope tag requests.

43. The method of clause 41, wherein the request for a plurality of epitope tagged biomolecule reagents comprises a single biomolecule request and plurality of epitope tag requests.

44. The method of clause 41, wherein the request for a plurality of epitope tagged biomolecule reagents comprises a plurality of biomolecule requests and a single epitope tag request.

45. The method of any one of clauses 35 to 44, wherein the received epitope tagged biomolecule reagent is sealed in a container.

46. The method of any one of clauses 35 to 44, wherein the biomolecule is a compound selected from the group consisting of a polypeptide, a nucleic acid and a polysaccharide.

47. The method of clause 46, wherein the nucleic acid is an oligonucleotide, DNA or RNA.

48. The method of clause 46, wherein the biomolecule is an oligonucleotide.

49. The method of clause 46, wherein the polypeptide is a protein, an enzyme or an antibody.

50. The method of clause 46, wherein the biomolecule is an antibody.

51. The method of any one of clauses 35 to 50, wherein the epitope tag is a polypeptide.

52. The method of clause 51, wherein the polypeptide ranges in length from 1 to 100,000 amino acid residues.

53. A method comprising:
communicating a request for a epitope tagged biomolecule reagent to a system comprising:
an input manager that receives an epitope tagged biomolecule reagent request;
a memory for storing a dataset comprising a plurality of epitope tagged biomolecule storage identifiers;
a processing module communicatively coupled to the memory and configured to identify one or more epitope tagged biomolecule storage identifiers from the dataset that corresponds to the components of the epitope tagged biomolecule reagent request;
an output manager for providing the identified epitope tagged biomolecule storage identifiers; and
receiving an epitope tagged biomolecule reagent comprising a biomolecule covalently coupled to an epitope tag.

54. The method of clause 53, wherein the request for an epitope tagged biomolecule reagent comprises a biomolecule request and an epitope tag request.

55. The method of any one of clauses 53 to 54, wherein the memory comprises a first dataset comprising a plurality of biomolecule storage identifiers for a plurality of activated biomolecules and a second dataset comprising a plurality of epitope tag storage identifiers for a plurality of activated epitope tags.

56. The method of any one of clauses 53 to 55, wherein communicating the request for an epitope tagged biomolecule reagent comprises inputting one or more of: an epitope tagged biomolecule request, a biomolecule request and an epitope tag request into a graphical user interface operatively coupled to the input manager.

57. The method of clause 56, wherein the graphical user interface comprises an internet website menu interface.

58. The method of any one of clauses 53 to 57, wherein the method comprises communicating a request for a plurality of epitope tagged biomolecule reagents.

59. The method of clause 58, wherein the request for the plurality of epitope tagged biomolecule reagents comprises a plurality of biomolecule requests and a plurality of epitope tag requests.

60. The method of clause 58, wherein the request for the plurality of epitope tagged biomolecule reagents comprises a single biomolecule request and plurality of epitope tag requests.

61. The method of clause 58, wherein the request for the plurality of epitope tagged biomolecule reagents comprises a plurality of biomolecule requests and a single epitope tag request.

62. The method of any one of clauses 53 to 61, wherein the received epitope tagged biomolecule reagent is sealed in a container.

63. The method of any one of clauses 53 to 62, wherein the biomolecule is a compound selected from the group consisting of a polypeptide, a nucleic acid and a polysaccharide.

64. The method of clause 63, wherein the nucleic acid is an oligonucleotide, DNA or RNA.

65. The method of clause 64, wherein the biomolecule is an oligonucleotide.

66. The method of clause 63, wherein the polypeptide is a protein, an enzyme or an antibody.

67. The method of clause 66, wherein the biomolecule is an antibody.

68. The method of any one of clauses 53 to 67, wherein the epitope tag is a polypeptide.

69. The method of clause 68, wherein the epitope tag is a polypeptide ranging in length from 1 to 100,000 amino acid residues.

70. A method comprising:
receiving a request for an epitope tagged biomolecule reagent, the request comprising one or more of:
an epitope tagged biomolecule request; and
a biomolecule request and an epitope tag request;
preparing an epitope tagged biomolecule reagent corresponding to the epitope tagged biomolecule reagent request by contacting an activated biomolecule with an activated epitope tag to produce the epitope tagged biomolecule reagent, wherein the preparing comprising selecting an activated biomolecule and an activated epitope tag from a storage comprising a plurality of activated biomolecules and a plurality of activated epitope tags.

71. The method of clause 70, wherein the method comprises receiving a request for a plurality of epitope tagged biomolecule reagents.

72. The method of clause 71, wherein the request for a plurality of epitope tagged biomolecule reagents comprises a plurality of biomolecule requests and a plurality of epitope tag requests.

73. The method of clause 71, wherein the request for a plurality of epitope tagged reagents comprises a single biomolecule request and plurality of epitope tag requests.

74. The method of clause 71, wherein the request for a plurality of epitope tagged biomolecule reagents comprises a plurality of biomolecule requests and a single epitope tag request.

75. The method of any one of clauses 70 to 74, wherein contacting comprises manually combining the activated biomolecule with the activated epitope tag in a contacting apparatus.

76. The method of clause 75, wherein the contacting apparatus is a microtube.

77. The method of any one of clauses 70 to 76, wherein the activated biomolecule and the activated epitope tag are contacted in a contacting apparatus of a reagent preparatory apparatus by a computer-controlled sampling device.

78. The method of any one of clauses 70 to 77, further comprising purifying the epitope tagged biomolecule reagent.

79. The method of any one of clauses 70 to 78, further comprising transporting the epitope tagged biomolecule reagent to a remote location.

80. The method of any one of clauses 70 to 79, wherein the request for an epitope tagged biomolecule reagent is received through an internet website.

81. The method of any one of clauses 70 to 80, wherein the request for an epitope tagged biomolecule reagent is received over the telephone.

82. The method of any one of clauses 70 to 81, wherein the request for an epitope tagged biomolecule reagent is received through the mail.

83. The method of any one of clauses 70 to 82, wherein the request for an epitope tagged biomolecule reagent is received through electronic mail.

84. The method of any one of clauses 70 to 83, further comprising providing a recommendation for an alternative epitope tagged biomolecule when the epitope tagged biomolecule corresponding to the request is not available.

85. The method of any one of clauses 70 to 84, further comprising providing a recommendation for an alternative biomolecule when the biomolecule that corresponds to the biomolecule request is not available.

86. The method of any one of clauses 70 to 85, further comprising providing a recommendation for an alternative epitope tag when the epitope tag that corresponds to the epitope tag request is not available.

87. The method of any one of clauses 70 to 86, wherein the biomolecule is a compound selected from the group consisting of a polypeptide, a nucleic acid and a polysaccharide.

88. The method of clause 87, wherein the nucleic acid is an oligonucleotide, DNA or RNA.

89. The method of clause 88, wherein the biomolecule is an oligonucleotide.

90. The method of clause 87, wherein the polypeptide is a protein, an enzyme or an antibody.

91. The method of clause 90, wherein the biomolecule is an antibody.

92. The method of any one of clauses 70 to 91, wherein the epitope tag is a polypeptide.

93. The method of clause 92, wherein the epitope tag is a polypeptide ranging in length from 1 to 100,000 amino acid residues.

94. A method comprising:
    receiving a request for an epitope tagged biomolecule reagent with a system comprising:
    an input manager that receives an epitope tagged biomolecule reagent request;
    a memory for storing a dataset comprising a plurality of epitope tagged biomolecule storage identifiers;
    a processing module communicatively coupled to the memory and configured to identify one or more epitope tagged biomolecule storage identifiers from the dataset that corresponds to the components of the epitope tagged biomolecule reagent request;
    an output manager;
    identifying the epitope tagged biomolecule storage identifier that corresponds with the epitope tagged biomolecule reagent request;
    outputting the identified epitope tagged biomolecule reagent storage identifier.

95. The method of clause 94, wherein the request for an epitope tagged biomolecule reagent comprises a biomolecule request and an epitope tag request.

96. The method of any one of clauses 94 to 95, further comprising displaying the outputted epitope tagged biomolecule reagent storage identifier onto an electronic display.

97. The method of any one of clauses 94 to 96, further comprising printing the outputted epitope tagged biomolecule reagent storage identifier.

98. The method of any one of clauses 94 to 97, wherein the method comprises receiving a plurality of requests for epitope tagged biomolecule reagents.

99. The method of clause 98, wherein the plurality of requests are received from the same user.

100. The method of clause 98, wherein the plurality of requests are received from different users.

101. The method of clause 98, wherein the request for the epitope tagged biomolecule reagents comprises a plurality of biomolecule requests and a plurality of epitope tag requests.

102. The method of clause 98, wherein the request for the epitope tagged biomolecule reagents comprises a single biomolecule request and plurality of epitope tag requests.

103. The method of any one of clauses 94 to 102, wherein the request for the epitope tagged biomolecule reagents comprises a plurality of biomolecule requests and a single epitope tag request.

104. The method of clause 103, further comprising contacting an activated biomolecule associated with biomolecule storage identifier with an activated epitope tag associated with the epitope tag storage identifier to produce the epitope tagged biomolecule reagent.

105. The method of clause 104, wherein contacting comprises manually combining the activated biomolecule with the activated epitope tag in a contacting apparatus.

106. The method of clause 105, wherein the contacting apparatus is a microtube.

107. The method of clause 105, wherein the activated biomolecule and the activated epitope tag are contacted in a contacting apparatus of a reagent preparatory apparatus by a computer controlled sampling device.

108. The method of clause 105, further comprising purifying the epitope tagged biomolecule reagent.

109. The method of any one of clauses 94 to 108, further comprising transporting the epitope tagged biomolecule reagent to a remote location.

110. The method of any one of clauses 94 to 109, wherein the request for an epitope tagged biomolecule reagent is received through an internet website.

111. The method of any one of clauses 94 to 110, wherein the request for an epitope tagged biomolecule reagent is received over the telephone and inputted into the input manager.

112. The method of any one of clauses 94 to 111, wherein the request for an epitope tagged biomolecule reagent is received through the mail and inputted into the input manager.

113. The method of clause 112, wherein the request for an epitope tagged biomolecule reagent is received through electronic mail and inputted into the input manager.

114. The method of any one of clauses 94 to 113, further comprising providing a recommendation for an alternative epitope tagged biomolecule from a database when a epitope tagged biomolecule storage identifier that corresponds to the epitope tagged biomolecule request is not available.

115. The method of any one of clauses 94 to 114, further comprising providing a recommendation for an alternative biomolecule from a database when a biomolecule storage identifier that corresponds to the biomolecule request is not available.

116. The method of any one of clauses 94 to 115, further comprising providing a recommendation for an alternative epitope tag from a database when an epitope tag storage identifier that corresponds to the epitope tag request is not available.

117. The method of any one of clauses 94 to 116, wherein the biomolecule is a compound selected from the group consisting of a polypeptide, a nucleic acid and a polysaccharide.

118. The method of clause 117, wherein the biomolecule is a nucleic acid.

119. The method of clause 118, wherein the nucleic acid is an oligonucleotide, DNA or RNA.

120. The method of clause 119, wherein the biomolecule is an oligonucleotide.

121. The method of clause 117, wherein the polypeptide is a protein, an enzyme or an antibody.

122. The method of clause 121, wherein the biomolecule is an antibody.

123. The method of any one of clauses 94 to 122, wherein the epitope tag is polypeptide.

124. The method of clause 123, wherein the epitope tag is a polypeptide ranging in length from 1 to 100,000 amino acids.

125. A system comprising:
 a plurality of activated biomolecules;
 a plurality of activated epitope tags; and
 a reagent preparatory apparatus for preparing an epitope tagged biomolecule reagent, wherein the reagent preparatory apparatus is configured to:
  receive an identified biomolecule storage identifier and epitope tag storage identifier; and
  produce an epitope tagged biomolecule reagent corresponding to the received biomolecule storage identifier and the epitope tag storage identifier.

126. The system of clause 125, wherein the reagent preparatory apparatus comprises a sampling device configured to provide an activated biomolecule and an activated epitope tag to a contacting apparatus.

127. The system of clause 126, wherein the reagent preparatory apparatus comprises a contacting apparatus configured for contacting the activated biomolecule with the activated epitope tag to produce the epitope tagged biomolecule reagent.

128. The system of clause 127, further comprising an epitope tagged biomolecule reagent analyzer.

129. The system of clause 128, wherein the analyzer comprises a purification component for purifying the epitope tagged biomolecule reagent.

130. The system of any one of clauses 125 to 126, wherein the system comprises a reagent packaging unit configured to seal the produced epitope tagged biomolecule reagent in a container.

131. The system of any one of clauses 125 to 130, wherein the reagent preparatory apparatus is operatively coupled to a system for receiving an epitope tagged biomolecule reagent request, the system comprising:
 an input manager for receiving a biomolecule request and an epitope tag request for an epitope tagged biomolecule reagent;
 a memory for storing a first dataset comprising a plurality of biomolecule storage identifiers for a plurality of activated biomolecules and a second dataset comprising a plurality of epitope tag storage identifiers for a plurality of activated epitope tags;
 a processing module communicatively coupled to the memory and configured to identify a biomolecule storage identifier and an epitope tag storage identifier from the first dataset and second dataset that correspond to the biomolecule request and epitope tag request;
 an output manager for providing the identified biomolecule storage identifier and an epitope tag storage identifier.

132. The system of any one of clauses 125 to 131, wherein the system comprises 1000 or more different activated biomolecules.

133. The system of any one of clauses 125 to 132, wherein the biomolecule is selected from the group consisting of a polypeptide, a nucleic acid and a polysaccharide.

134. The system of clause 133, wherein the biomolecule is an oligonucleotide.

135. The system of clause 134, wherein the system comprises 1000 or more different types of oligonucleotides.

136. The system of clause 133, wherein the biomolecule is an antibody.

137. The system of clause 136, wherein the system comprises 1000 or more different types of antibodies.

138. The system of any one of clauses 125 to 137, wherein each activated biomolecule comprises a reactive linker.

139. The system of any one of clauses 125 to 138, wherein the system comprises 100 or more different activated epitope tags.

140. The system of clause 139, wherein the epitope tag comprises a polypeptide.

141. The system of any one of clauses 125 to 140, wherein activated epitope tag comprises a reactive linker.

142. A storage comprising:
 a plurality of activated biomolecules; and
 a plurality of activated epitope tags.

143. The storage of clause 142, wherein the storage comprises 1000 or more different activated biomolecules.

144. The storage of any one of clauses 142 to 143, wherein the biomolecule is selected from the group consisting of a polypeptide, a nucleic acid and a polysaccharide.

145. The storage of clause 144, wherein the biomolecule is an oligonucleotide.

146. The storage of clause 145, wherein the storage comprises 1000 or more different types of oligonucleotides.

147. The storage of clause 144, wherein the biomolecule is an antibody.

148. The storage of clause 147, wherein the storage comprises 1000 or more different types of antibodies.

149. The storage of any one of clauses 142 to 148, wherein each activated biomolecule comprises a reactive linker.

150. The storage of any one of clauses 142 to 149, wherein the storage comprises 100 or more different activated epitope tags.

151. The storage of clause 150, wherein the epitope tag comprises a polypeptide.

152. An epitope tagged biomolecule reagent dispensing system comprising:
 an input module for receiving a request for an epitope tagged biomolecule;
 a reagent preparatory apparatus; and
 a dispensing module for outputting a packaged epitope tagged biomolecule.

153. The epitope tagged biomolecule reagent dispensing system of clause 152, wherein the input module comprises:

a graphical user interface for communicating an epitope tagged biomolecule request to an input manager;

an input manager for receiving a request for an epitope tagged biomolecule;

a memory for storing a dataset having a plurality of storage identifiers that correspond to the one or more components of the epitope tagged biomolecule reagent request;

a processing module communicatively coupled to the memory and configured to identify a storage identifier from the dataset that corresponds to the components of the epitope tagged biomolecule reagent request; and an output manager for providing the identified storage identifiers.

154. The epitope tagged biomolecule reagent dispensing system of any one of clauses 152 to 153, wherein the reagent preparatory apparatus comprises one or more of a source of a epitope tagged biomolecule, a source of a biomolecule, a source of an epitope tag, a source of a reactive linker, a source of an activated biomolecule and a source of an activated epitope tag.

155. The epitope tagged biomolecule reagent dispensing system of any one of clauses 152 to 154, wherein the reagent preparatory apparatus comprises:

a sampling device configured to provide an activated biomolecule and an activated epitope tag to a contacting apparatus.

156. The epitope tagged biomolecule reagent dispensing system of clause 155, further comprising a contacting apparatus configured for contacting the activated biomolecule with the activated epitope tag to produce the epitope tagged biomolecule reagent.

157. The epitope tagged biomolecule reagent dispensing system of any one of clauses 155 to 156, further comprising an epitope tagged biomolecule reagent analyzer.

158. The epitope tagged biomolecule reagent dispensing system of clause 157, wherein the analyzer comprises a purification component for purifying the epitope tagged biomolecule reagent.

159. The epitope tagged biomolecule reagent dispensing system of clause 158, wherein the purification component comprises liquid chromatography.

160. The epitope tagged biomolecule reagent dispensing system of any one of clauses 153 to 159, further comprising a solvent chamber configured to provide one or more solvents to the contacting apparatus.

161. The epitope tagged biomolecule reagent dispensing system according to any one of clauses 152 to 160, wherein the dispensing module comprises a reagent packaging unit configured to seal the produced epitope tagged biomolecule reagent in the container.

162. The epitope tagged biomolecule reagent dispensing system according to clause 161, wherein the container is selected from the group consisting of a pouch, bag, tube, vial, microtube or bottle.

163. The epitope tagged biomolecule reagent dispensing system according to clause 161, wherein the packaging unit is further configured to dispense the sealed container with epitope tagged biomolecule in a second container.

164. The epitope tagged biomolecule reagent dispensing system according to clause 163, wherein the second container is selected from the group consisting of a pouch, bag, tube, vial, microtube or bottle.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for use in preparing an epitope tagged biomolecule reagent, the system comprising:

an input manager for receiving a request for an epitope tagged biomolecule reagent, wherein the request for an epitope tagged biomolecule reagent comprises a biomolecule request and an epitope tag request;

a memory for storing a dataset comprising a plurality of epitope tagged biomolecule storage identifiers, wherein the memory comprises a first dataset comprising a plurality of biomolecule storage identifiers for a plurality of activated biomolecules and a second dataset comprising a plurality of epitope tag storage identifiers for a plurality of activated epitope tags;

a processing module communicatively coupled to the memory and configured to identify one or more epitope tagged biomolecule storage identifiers from the dataset that corresponds to the components of the epitope tagged biomolecule reagent request;

an output manager for providing the identified epitope tagged biomolecule storage identifiers; and a reagent preparatory apparatus for preparing the epitope tagged biomolecule reagent, wherein the reagent preparatory apparatus is operatively coupled to the output manager and is configured to:

receive the identified biomolecule storage identifier and epitope tag storage identifier; and produce an epitope tagged biomolecule reagent corresponding to the received biomolecule storage identifier and the epitope tag storage identifier.

* * * * *